US008207130B2

(12) United States Patent
Epstein et al.

(10) Patent No.: US 8,207,130 B2
(45) Date of Patent: Jun. 26, 2012

(54) COMBINATION CANCER IMMUNOTHERAPY WITH CO-STIMULATORY MOLECULES

(75) Inventors: Alan Epstein, La Canada, CA (US); Peishing Hu, Covina, CA (US)

(73) Assignee: University of Southern California, Los Angeles, CA (US)

( * ) Notice: Subject to any disclaimer, the term of this patent is extended or adjusted under 35 U.S.C. 154(b) by 143 days.

(21) Appl. No.: 12/732,147

(22) Filed: Mar. 25, 2010

(65) Prior Publication Data

US 2011/0002921 A1 Jan. 6, 2011

Related U.S. Application Data

(62) Division of application No. 11/262,286, filed on Oct. 28, 2005, now Pat. No. 7,696,175.

(60) Provisional application No. 60/623,849, filed on Oct. 29, 2004.

(51) Int. Cl.
*A61K 38/16* (2006.01)
(52) U.S. Cl. ..................................... 514/21.2
(58) Field of Classification Search .................. None
See application file for complete search history.

(56) References Cited

U.S. PATENT DOCUMENTS

| | | | |
|---|---|---|---|
| 4,816,567 A | 3/1989 | Cabilly et al. | |
| 4,956,778 A | 9/1990 | Naito | |
| 5,091,513 A | 2/1992 | Huston et al. | |
| 5,116,943 A | 5/1992 | Koths et al. | |
| 5,132,405 A | 7/1992 | Huston et al. | |
| 5,565,332 A | 10/1996 | Hoogenboom et al. | |
| 6,312,700 B1 | 11/2001 | Weinberg | |
| 6,331,415 B1 | 12/2001 | Cabilly et al. | |
| 6,827,925 B1 | 12/2004 | Williams et al. | |
| 7,696,175 B2 * | 4/2010 | Epstein et al. ............... | 514/19.3 |
| 2002/0086014 A1 | 7/2002 | Korman et al. | |
| 2004/0228836 A1 | 11/2004 | Epstein et al. | |

FOREIGN PATENT DOCUMENTS

| | | |
|---|---|---|
| CN | 1217750 | 5/1999 |
| WO | WO-00/01822 | 1/2000 |

OTHER PUBLICATIONS

Chinese Office Action dated Jul. 9, 2010 for Application No. 200580042109.0.
Partial European Search Report dated Jul. 25, 2011 from related patent application No. 11158453.8-2401.
Li Jiali et al., "Complete Regression of Experimental Solid Tumors by Combination LEC/chTNT-3 Immunotherapy and CD25 T-Cell Depletion", Cancer Research, American Association for Cancer Research, Baltimore, MD., US, vol. 63, No. 23, Dec. 1, 2003, pp. 8384-8392.
Liu Aihong et al., "Combination B7-Fc Fusion Protein Treatment and Treg Cell Depletion Therapy", Clincal Cancer Research: An Official Journal of the American Association For Cancer Research, Dec. 1, 2005, vol. 11, No. 23, pp. 8492-8502.
Sturmhoefel K et al., "Potent Activity of Soluble B7-IGG Fusion Proteins in Therapy of Established Tumors and as Vaccine Adjuvant", Cancer Research, American Association for Cancer Research, Baltimore, MD., US, vol. 59, No. 19, Oct. 1, 1999, pp. 4964-4972.
Yamaguchi Nobuya et al., "Induction of Tumor Regression by Administration of B7-IG Fusion Proteins: Mediation by Type 2 Production", Journal of Immunology, vol. 172, No. 3, Feb. 1, 2004, pp. 1347-1354.
Alderson et al., Molecular and biological characterization of human 4-1BB and its ligand; *Eur. J. Immunol.*, 24(9):2219-27 (1994).
Altschul et al., Gapped BLAST and PSI-BLAST: a new generation of protein database search programs; Nucl. Acids Res., 25:3389-3402 (1977).
Altschul et al., Basic Local Alignment Search Tool. J. Mol. Biol., 215:403-410 (1990).
Aluvaihare et al., Regulatory T-cells mediate maternal tolerance to the fetus; Nature Immunol., 5:266-271 (2004).
Blattman et al.,. Cancer immunotherapy: A treatment for the masses; Science, 305:200-205 (2004).
Blazer et al., Infusion of Anti-B7.1 (CD80) and Anti-B7.2 (CD86) Monoclonal Antibodies Inhibits Murine Graft-Versus-Host Disease Lethality in Part Via Direct Effects on DC4$^+$ and CD8$^+$ T Cells$^1$, Journal of Immunology 1996, 157:3250-3259.
Bruder et al., Neuropilin-1: a surface marker of regulatory T-cells; Eur. J. Immunology, 34:623-630 (2004).
Challita-Eid et al., A B7.1-Antibody Fusion Protein Retains Antibody Specificity and Ability to Activate Via the T Cell Costimulatory Pathway; *J. Immunol.*, 160: 3419-3426 (1998).
Chen, L., Co-Inhibitory Molecules of the B7-CD28 Family in the Control of T-cell Immunity; Nature Reviews: Immunology, 4:336-347 (2004).
Curiel et al., Specific recruitment of regulatory T cells in ovarian carcinoma fosters immune privilege and predicts reduced survival; Nature Med., 10:942-949 (2004).
Dy et al., Novel Targets for Lung cancer Therapy: Part I; J. Clin. Oncol. 20: 2881-2894 (2002).
Egen et al., CTLA-4: New insights into its biological function and use in tumor immunotherapy. Nature Immunol., 3:611-618 (2002).
Epstein et al., A Novel Method for the Detection of Necrotic Lesions in Human Cancers; *Cancer Res.*, 48:5842-5848 (1988).
Fields et al., B7.1 is a Quantitatively Stronger Costimulus Than B7.2 in the Activation of Naïve CD8+ TCR-Transgenic T-cells; J. Immunol., 161:5268-5275, (1998).
Francis et al., PEGylation of cytokines and other therapeutic proteins and peptides: the importance of biological optimization of coupling techniques; Int. J. Hematol., 68: 1-18 (1998).

(Continued)

*Primary Examiner* — Ilia Ouspenski
(74) *Attorney, Agent, or Firm* — Foley & Lardner LLP; Antoinette F. Konski

(57) ABSTRACT

Provided are methods of reducing the size of a tumor or inhibiting the growth of cancer cells in an individual or inhibiting the development of metastatic cancer by administering an effective amount of a soluble form of a co-stimulatory molecule from an antigen presenting cell and by reducing the activity of immunoregulatory T cells in the individual. Methods of reduction in the activity of immunoregulatory T cells involve removing them ex vivo or depleting or inactivating them in vivo. Also provided are cancer therapeutic compositions comprising a soluble form of a co-stimulatory molecule from an antigen presenting cell and an antibody specific for an intracellular antigen.

22 Claims, 7 Drawing Sheets

OTHER PUBLICATIONS

Frankel et al., The Rapid Determination of Binding Constants for Antiviral Antibodies by a Radioimmunoassay. An Analysis of the Interaction Between Hybridoma Proteins and Influenza Virus; *Mol. Immunol.*, 16: 101-106 (1979).

Freeman et al., B7, A New Member of the Ig Superfamilly with Unique Expression on Activated and Neoplastic B Cells; *J. Immunol.*, 143:2714-2722 (1989).

Gerstmayer, et al., Costimulation of T-cell proliferation by a chimeric B7-antibody fusion protein. *Cancer Immunol. Immunother.*, 45: 156-158 (1997).

Godfry et al., Identification of a Human OX-40 Ligand, a Costimulator of $CD4^+$ T Cells with Homology to Tumor Necrosis Factor; J. Exp. Med. 180(2):757-62 (1994).

Golgher et al., Depletion of $CD25^+$ regulatory cells uncovers immune responses to shared murine tumor rejection antigens. Eur. J. Immunol., 32:3267-3275 (2002).

Greenwald et al., The B7 Family Revisited, Annu. Rev. Immunol. 2005, 23:515-48.

Gura, Cancer Models: Systems for Identifying New Drugs are Often Faulty, Science, 1997, 278:1041-1042.

Henikoff et al., Amino acid substitution matrices from protein blocks; Proc. Natl. Acad. Sci. USA, 89:10915 (1989).

Hodi et al., Biologic activity of cytotoxic T lymphocyte-associated antigen 4 antibody blockade in previously vaccinated metastatic melanoma and ovarian carcinoma patients; Proc. Natl. Acad. Sci. (USA), 100:4712-4717 (2003).

Holliger et al., Carcinoembryonic Antigen (CEA)-specific T-Cell Activation in Colon carcinoma induced by Anti-CD3x Anti-CEA Bispecific Diabodies and B7 x Anti-CEA Bispecific Fusion Proteins. Cancer Res., 59(12):2909-16 (1999).

Hornick et al., A New Chemically Modified Chimeric TNT-3/B, Monoclonal Antibody Directed Against DNA for the Radioimmunotherapy of Solid Tumors; Cancer Biotherapy and Radiopharmaceuticals, 13:255-268, (1998).

Huston et al., Protein engineering of antibody binding sites: Recovery of specific activity in an antigen-digoxin single-chain FV analogue produced bin *Escherichia coli*; Proc. Nat. Acad. Sci. USA, 85:5879-5883 (1988).

Ichihara et al. Increased Populations of Regulatory T Cells in Peripheral Blood and Tumor-Infiltrating Lymphocytes in Patients with Gastric and Esophageal Cancers; Clin. Cancer Res., 9:4404-4408 (2003).

International Search Report for International PCT Application No. PCT/US2005/039102 dated Oct. 20, 2006.

Javia, et al., $CD4^+CD25^+$ Suppressor Lymphocytes in the Circulation of Patients Immunized Against Melanoma Antigens; J. Immunother., 26:85-93, (2003).

June C.H., Can't Get Any Help? New Approaches for Adoptive Immunotherapy of Cancer; J. Immunotherapy, 24(5): 389-391 (2001).

Karlin et al., Applications and statistics for multiple high-scoring segments in molecular sequence; Proc. Natl. Acad. Sci. USA, 90:5873-5877 (1993).

Katre et al., Immunogenicity of Recombinant IL-2 Modified by Covalent Attachment of Polyethylene Glycol; J. Immunol., 144, 209-213 (1990).

Kim et al., Constitutive and Cytokine-Induced GITR Ligand Expression on Human Retinal Pigment Epithelium and Photoreceptors; Invest. Ophthalmol. Vis. Sci., 45 (9), 3170-3176 (2004).

Leach et al., Enhancement of Antitumor Immunity by CTLA-4 Blockade; Science, 271:1734-1736 (1996).

Li J. et al, "Complete regression of experimental solid tumors by combination LEC/chTNT-3 immunotherapy and $CD25^+$ T-cell depletion," Cancer Research, American Association for Cancer Research, Baltimore, MD., US, vol. 63, No. 23, (Dec. 1, 2003), pp. 8384-8392.

Li et al., Complete Regression of Experimental Solid Tumors by Combination LEC/hTNT-3 Immunotherapy and $CD25^+$ T-Cell Depletion; *Cancer Res.*, 63:8384-92 (2003).

Li et al., A. LEC/chTNT-3 Fusion Protein for the Immunotherapy of Experimental Solid Tumors. J. Immunother., 26: 320-331 (2003).

Liu A. et al, "Combination B7-Fc fusion protein treatment and Treg cell depletion therapy," Clinical Cancer Research an Official Journal of the American Association for Cancer Research Dec. 1, 2005, vol. 11, No. 23, pp. 8492-8502.

Liyanage et al., Prevalence of Regulatory T Cells Is Increased in Peripheral Blood and Tumor Microenvironment of Patients with Pancreas or Breast Adenocarcinoma; J. Immunol., 169:2756-2761 (2002).

Lum et al., Immune Modulation in Cancer Patients After Adoptive Transfer of Anti-CD3/Anti-CD28-Costimulated T Cells-Phase I Clinical Trial; J. Immunother., 24:408-19 (2001).

Lyons, Analysing cell division in vivo and in vitro using flow cytometric measurement of CFSE dye dilution; *J. Immunol. Meth.*, 243: 147-154 (2000).

Marshall et al., Immunosuppressive regulatory T cells are abundant in the reactive lymphocytes of Hodgkin's lymphoma; Blood, 103:1755-1762 (2004).

McHugh et al., Construction, purification, and functional incorporation on tumor cells of glycolipid-anchored human B7-1 (CD80); *Proc. Natl. Acad. Sci.*, 92: 8059-8063 (1995).

McHugh et al., Protein Transfer of Glycosyl-phosphatidylinositol-B7-1 into Tumor Cell Membranes: A Novel Approach to Tumor Immunotherapy; Cancer Research, 59:2433-2437 (1999).

Meiser et al., Chimeric Monoclonal CD4 Antibody—A Novel Immunosuppressant for Clinical Heart Transplantation ; Transplantation, 58(4): 419-23 (1994).

Mocellin et al., Adjuvant immunotherapy for solid tumors: from promise to clinical application; Cancer Immunol. & Immunother., 51: 583-595 (2002).

Needleman et al., A General Method Applicable to the Search for Similarities in the Amino Acid Sequence of Two Proteins; J. Mol. Biol., 48:443 (1970).

North et al., Elimination of cycling $CD4^+$ suppressor T cells with an anti-mitotic drug releases non-cycling $CD8^+$ T cells to cause regression of an advanced lymphoma; Immunology, 71:90-95 (1990).

Nomiyama et al. Human CC chemokine liver-expressed chemokine/CCL16 is a functional ligand for CCR1, CCR2, and CCR5, and constitutively expressed by hepatocytes; Intl. Immunol., 13:1021-1029 (2001).

Onizuka et al., Tumor Rejection by in Vivo Administration of Anti-CD25 (Interleukin-2 Receptor $\alpha$) Monoclonal Antibody; Cancer Res., 59:3128-3133 (1999).

Pardoll, D., Does the Immune System See Tumors as Foreign or Self?; Annu. Rev. Immunol., 21:807-839 (2003).

Parish, CR., Cancer immunotherapy: The past, the present, and the future; Immunol. Cell Biol., 81:106-113 (2003).

Park et al., Targeting and Blocking B7 Costimulatory Molecues on Antigen-Presenting Cells Using CTLA4Ig-Conjugated Liposomes: In Vitro Characterization and in Vivo Factors Affecting Biodistribution; Pharm Res., 20(8):1239-48 (2003).

Pearson et al., Improved tools for biological sequence comparison; Proc. Nat'l. Acad. Sci. USA, 85:2444 (1988).

Phan et al., Cancer regression and autoimmunity induced by cytotoxic T lymphocyte-associated antigen 4 blockade in patients with metastatic melanoma; Proc. Natl. Acad. Sci. USA, 100:8372-8377, (2003).

Runyon et al., The combination of chemotherapy and systemic immunotherapy with soluble B7-immunoglobulin G leads to cure of murine leukemia and lymphoma and demonstration of tumor-specific memory responses; Blood, 97:2420-2426 (2001).

Sturmhoefel K. et al, "Potent Activity of Soluble B7-IgG Fusion Proteins in Therapy of Established Tumors and As Vaccine Adjuvant", Cancer Research, American Association for Cancer Research, Baltimore, MD., US, vol. 59, No. 19, Oct. 1, 1999.

Sakaguchi et al. Immunologic Self-Tolerance Maintained by Activated T Cells Expressing IL-2 Receptor $\alpha$-Chains (CD25) Breakdown of a single mechanism of self-tolerance causes various autoimmune diseases. J. Immunol., 155:1151-1164 (1995).

Seko et al., Expression of Costimulatory Molecules (4-1BBL and Fas) and Major Histocompatibility Class I Chain-Related A (MICA) in Aortic Tissue with Takayasu's Arteritis; J. Vasc. Res., 41 (1); 84-90 (2004).

Seo et al., Depletion of IL-10- and TGF-$\beta$-Producing Reguatory $\gamma\delta$ T Cells by Administering a Daunomycin-Conjugated Specific Monoclonal Antibody in Early Tumor Lesions Augments the Activity of CTLs and NK Cells; J. Immunol., 163:242-249 (1999).

Sharifi et al., Characterization of a Phage Display-Derived Human Monoclonal Antibody (NHS76) Counterpart to Chimeric TNT-1 Directed Against Necrotic Regions of Solid Tumors; *Hybridoma Hybridomics*, 20:305-311 (2001).

Shevach et al., Control of T-cell activation by $CD4^+$ $CD25^+$ suppressor T cells; Immunol. Rev., 182:58-67 (2001).

Shimizu et al., Induction of Tumor Immunity by Removing $CD25^+$ $CD4^+$ T cells: A Common Basis Between Tumor Immunity and Autoimmunity; J. Immunol., 163: 5211-5218 (1999).

Singh et al. A Novel Approach to Cancer Immunotherapy: Tumor Cells Decorated with CD80 Generate Effective Antitumor Immunity; Cancer Res. 6:4067-4073 (2003).

Smith et al., M.S. Comparison of Biosequences; Adv. Appl. Math., 2:482-489 (1981).

Smyth et al., A fresh look at tumor immunosurveillance and immunotherapy; Nature Immunology, 2:293-299 (2001).

Stephens et al. Engagement of Glucocorticoid-Induced TNFR Family-Related Receptor on Effector T Cells by its Ligand Mediates Resistance to Suppression by $CD4^+$ $CD25^+$ T cells; J. Immunology. 173:5008-5020 (2004).

Sturmhoefel et al., Potent activity of Soluble B7-IgG Fusion Proteins in Therapy of Established Tumors and as Vaccine Adjuvant; Cancer Res., 59:4964-4972 (1999).

Tanaka et al., Depletion of $CD4^+$ $CD25^+$ Regulatory Cells Augments the Generation of Specific Immune T Cells in Tumor-Draining Lymph Nodes; J. Immunother., 25: 207-217 (2002).

Tone et al. Regulatiojn of CD40 function by its isoforms generated through alternative splicing; Proc. Natl. Acad. Sci. U.S.A., 98 (4): 1751-1756 (2001).

Tone et al., Mouse glucocorticoid-induced tumor necrosis factor receptor ligand is costimulatory for T cells; Proc. Natl. Acad. Sci. 100:15059-15064 (2003).

Townsend et al., Tumor Rejection After Direct Costimuation of $CD8^+$ T Cells by B7-Transfected Melanoma Cells; *Science*, 259:368-370 (1993).

Waldmann, TA. Immunotherapy: past, present, and future; Nature Med., 9:269-277 (2003).

Wilcox et al., Ligation of CD137 receptor prevents and reverses anergy of $CD8^+$ cytolytic T lymphocytes in vivo; Blood, 103:177-184 (2004).

Wines et al., The IgG Fc Contains Distinct Fc Receptor (FcR) Binidng Sites: The Leukocyte Receptors FcγRI and FcγRIIa Bind to a Region in the FC Distinct from That Recognized by Neonatal FcR and Protein A; *J. Immunol.*, 164(10):5313-8 (2000).

Woo et al., Cutting edge: Regulatory T cells from Lung Cancer Patients Directly Inhibit Autologous T Cell Proliferation; J. Immunol., 168:4272-4276 (2002).

Woo et al., Regulatory CD4+CD25+ T cells in Tumors from Patients with Early-Stage Non-Small Cell Lung Cancer and Late-Stage Ovarian Cancer; Cancer Res., 61:4766-4772 (2001).

Yamaguchi et al., Induction of Tumor Regression by Administration of B7-Ig Fusion Proteins: Mediation by Type 2 $CD8^+$ T Cells and Dependence on IL-4 Production; J. Immunol., 172:1347-54 (2004).

Yang et al., Antitumor Immunity Elicited by Tumor Cells Transfected with B7-2, a Second Ligand for CD28/CTLA-4 Costimulatory Molecules; *J. Immunol.*, 154:2794-2800 (1995).

Zhou et al., Intramuscular gene transfer of soluble $B7.1/IG_1$ fusion cDNA induces potent antitumor immunity as an adjuvant for DNA vaccination; Cancer Gene Ther., 10(6):491-99 (2003).

Extended European Search Report dated Nov. 14, 2011 for European Application No. 11158453.8.

US Office Action dated Nov. 30, 2011 for U.S. Appl. No. 12/732,140.

\* cited by examiner

A

B

COMBINATION CANCER IMMUNOTHERAPY WITH CO-STIMULATORY MOLECULES

CROSS REFERENCE TO RELATED PATENT APPLICATIONS

This application is a divisional of U.S. Ser. No. 11/262,286, filed Oct. 28, 2005, which claims priority under 35 U.S.C. §119(e) to U.S. provisional application Ser. No. 60/623,849, filed Oct. 29, 2004, incorporated herein by reference in its entirety.

FIELD OF THE INVENTION

The present invention relates to cancer immunotherapeutic methods.

BACKGROUND OF THE INVENTION

The following discussion of the background of the invention is merely provided to aid the reader in understanding the invention and is not admitted to describe or constitute prior art to the present invention.

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed. As key immunoregulatory molecules and signals of immunity are identified and prepared as therapeutic reagents, the clinical effectiveness of such reagents can be tested using well-known cancer models. Immunotherapeutic strategies include administration of vaccines, activated cells, antibodies, cytokines, chemokines, as well as small molecular inhibitors, anti-sense oligonucleotides, and gene therapy (Mocellin, et al., Cancer Immunol. & Immunother. (2002) 51: 583-595; Dy, et al., J. Clin. Oncol. (2002) 20: 2881-2894, 2002).

The growth and metastasis of tumors depends to a large extent on their capacity to evade host immune surveillance and overcome host defenses. Most tumors express antigens that can be recognized to a variable extent by the host immune system, but in many cases, the immune response is inadequate. Failure to elicit a strong activation of effector T-cells may result from the weak immunogenicity of tumor antigens or inappropriate or absent expression of co-stimulatory molecules by tumor cells. For most T-cells, proliferation and IL-2 production require a co-stimulatory signal during TCR engagement, otherwise, T-cells may enter a functionally unresponsive state, referred to as clonal anergy.

An important co-stimulatory signal directed through CD28 on T cells occurs via interaction with B7 and its family members including B7.1 (CD80) and B7.2 (CD86) expressed on antigen presenting cells (APC). B7.1, initially discovered as a B-cell antigen, has been shown to induce T cell-dependent rejection of B7-expressing tumors in mice and protect against tumor challenge with parental tumor cells. McHugh et al. 1999, demonstrated proliferation of cytotoxic T-cells in a mixed-lymphocyte-reaction using a recombinant glycol-lipid-anchored protein fused to the extracellular domain of human B7.1.

Previous studies described some success utilizing the B7/CD28 pathway in cancer immunotherapy. Most studies, however, utilized ex vivo genetic modifications of tumor cells to increase the expression of B7 through conventional approaches including transfection or transduction (see e.g., Townsend, et al, *Science* 259:368-370; Yang, et al., 1995. *J. Immunol.* 154:2794-2800). Zhou et al., (Cancer Gene Ther. 2003 June; 10(6):491-9) described cancer therapeutic effects following administration of vectors encoding B7.1-IgGFc and a separate vector encoding a tumor antigen, CEA.

Singh et al. (2003 *Cancer Res.* 6:4067-4073) used B7.1-streptavidin after modification of the tumor cell membrane with biotin to rapidly and durably display B7.1 on tumor cells. Other investigators have tried to anchor B7 on the tumor cell membrane by physical methods such as a recombinant glycol-lipid-anchored protein including the extracellular domains of human B7.1 (McHugh, et al., 1995 *Proc. Natl. Acad. Sci.* 92: 8059-8063). Challita-Eid, et al., (1998 *J. Immunol.* 160: 3419-3426) described a co-stimulator/antibody fusion protein involving B7.1 fused to an anti-HER2/neu antibody for use in treating tumors. Holliger et al., (Cancer Res. 1999 Jun. 15; 59(12):2909-16) described a B7.1-anti-CEA antibody fusion and its use for immunotherapy of CEA expressing cancers. Gerstmayer et al., (Cancer Immunol Immunother. 1997 November-December; 45(3-4):156-8) described a fusion protein of B7-2 and anti-cERB2 for treatment of adenocarcinomas.

T-regulatory cells ("T reg. cells" or "immunoregulatory T cells") are associated with the $CD4^+CD25^+$ phenotype and constitute 5-10% of circulating $CD4^+$ T-cells in humans and rodents. $CD4^+CD25^+$ T-reg cells are involved in T cell-mediated immunological self-tolerance. Specifically, in vivo injection of anti-CD25 antibody has been reported to regress leukemia and solid tumors in animal models (Onizuka, 1999). However, in most of these studies, T-reg depletion resulted in either incomplete tumor reduction or only a delay in the growth of well-established tumor implants.

Although much has been learned about controlling and directing an immune response, there is need for newer and more effective immunotherapeutic approaches to cancer therapy.

SUMMARY OF THE INVENTION

Provided are new cancer immunotherapeutic methods that combine administration of soluble co-stimulatory molecules with treatment to reduce immunoregulatory T cell activity in the individual.

Accordingly, a method of reducing the size of a tumor or inhibiting the growth of cancer cells in an individual or reducing or inhibiting the development of metastatic cancer in an individual suffering from cancer, is provided, which comprises administering a soluble form of a co-stimulatory molecule and reducing immunoregulatory T cell activity in the individual. The soluble form of the co-stimulatory molecule which is useful for this purpose is one that is derived from a co-stimulatory molecule expressed by an antigen presenting cell. In preferred embodiments, the soluble form of the co-stimulatory molecule is derived from B7, CD137-L, CD134-L, GITR-L or CD40.

In a preferred embodiment, the co-stimulatory molecule is B7, and more preferably, B7.1. The soluble form of the co-stimulatory molecule comprises one or more extracellular domains from the co-stimulatory molecule. In addition, the soluble form of the co-stimulatory molecule functions as a co-stimulator of T cell activation.

In another embodiment, the soluble form of the co-stimulatory molecule is linked to another protein. A linker may be present between the extracellular domain(s) of the co-stimulatory molecule and the other protein.

The other protein which can be linked to the soluble form of the co-stimulatory molecule can be an immunoglobulin fragment comprising the CH2 and CH3 domain or an immunoglobulin fragment comprising the hinge, or portion thereof and CH2 and CH3 domain.

In yet another embodiment, the soluble form of the co-stimulatory molecule is a homodimeric protein wherein each polypeptide of the homodimeric protein comprises the extracellular domain(s) of the co-stimulatory molecule and an immunoglobulin fragment comprising a hinge or portion thereof, CH2 and CH3 domain.

In still another embodiment, the soluble form of the co-stimulatory molecule is linked to an immunoglobulin Fc.

In yet another embodiment, the soluble form of the co-stimulatory molecule is linked to an antibody. In some embodiments, the antibody is a tetramer comprising two heavy and two light chains. The extracellular domain(s) of the co-stimulatory molecule can be linked to the variable region of each heavy chain of an antibody.

The antibody linked to the soluble co-stimulatory molecule can be specific for a tumor cell-surface antigen, a stromal component of a tumor, an intracellular antigen, or an intranuclear antigen. In the latter case, the antibody can be a murine, chimeric, humanized, or human form of murine antibody TNT-1, TNT-2, or TNT-3 or is NHS76.

Treatment that reduces immunoregulatory T cell activity in the individual can be achieved by removing ex vivo immunoregulatory T cells from the individual, or by administering an agent to the individual that depletes or inactivates immunoregulatory T cells. This treatment can be before, after or substantially simultaneously with the administration of the soluble form of the co-stimulatory molecule.

In one approach, at least one antibody that binds to immunoregulatory T cells is used to reduce the activity of immunoregulatory T cells in the individual. Such antibody preferably is selected from the group consisting of anti-CD4, anti-CD25, anti-neuropilin, and anti-CTLA4. The antibody can be a murine, chimeric, humanized, or human antibody.

The activity of immunoregulatory T cells in vivo may be reduced by administering a GITR ligand agonist.

In another embodiment, the method further comprises administering T cells which have cytotoxic activity against the tumor or cancer cells. This may be achieved by removing T cells from the individual, activating the T cells, and then administering the activated T cells back to the individual. In one embodiment, activation is achieved by exposure to IL-2 and/or anti-CD3 antibody. In another embodiment, ex vivo activation is achieved by exposure of the T cells to the cancer cells or to a cancer cell vaccine. Adoptive transfer of the T cells may occur before, during or after administering the soluble co-stimulatory molecule and/or treatment to reduce immunoregulatory T cell activity in the individual. Adoptive transfer is preferably given after removal, depletion or inactivation of immunoregulatory T cells.

Also provided are cancer therapeutic agents, comprising a soluble form of a co-stimulatory molecule selected from the group consisting of B7, CD137-L, CD134-L, GITR-L and CD40, wherein the soluble form of the co-stimulatory molecule is a fusion protein comprising one or more extracellular domains of the co-stimulatory molecule and an antibody, wherein the antibody is specific for an intracellular antigen. The soluble form of the co-stimulatory molecule is preferably B7.1.

In other embodiments, the antibody of the cancer therapeutic agent antibody is specific for an intranuclear antigen. In further embodiments, the anti-nuclear antigen specific antibody is a murine, chimeric, humanized, or human form of murine antibody TNT-1, TNT-2, or TNT-3, or is NHS76.

DETAILED DESCRIPTION OF THE INVENTION

Figure 1:
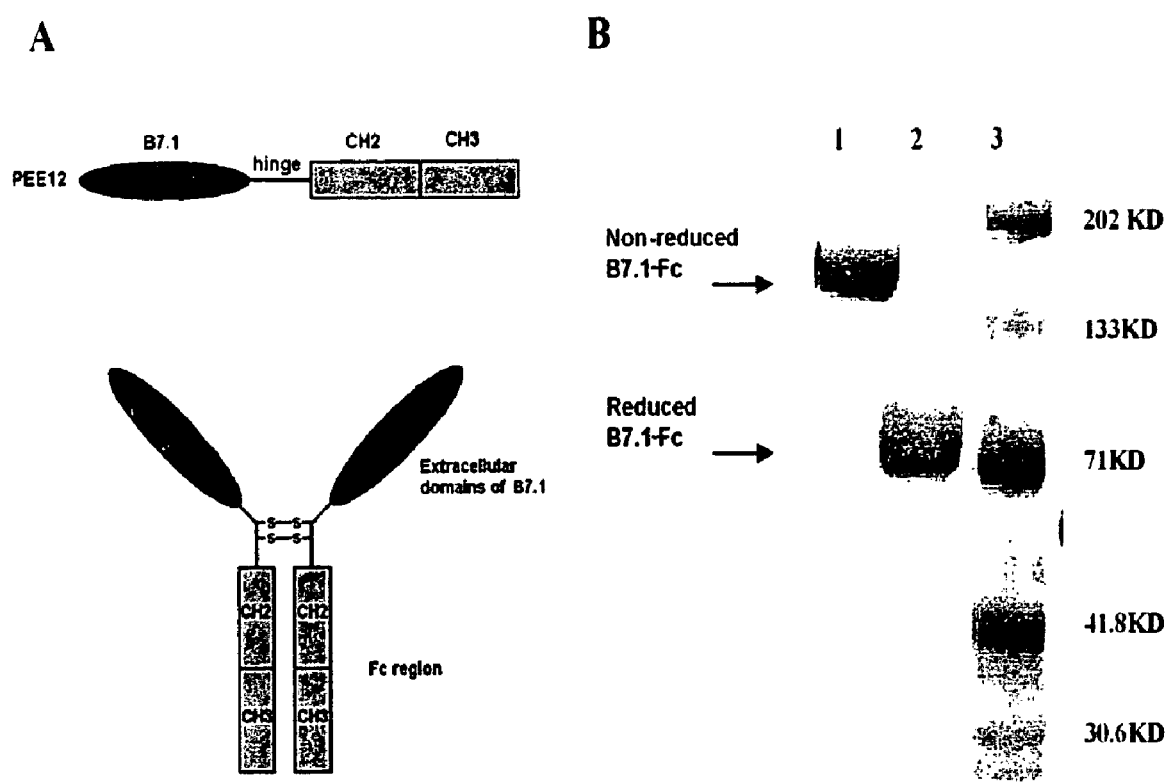
FIGS. 1A-B. 1A is a schematic diagram showing genetic construct and the resulting B7.1-Fc fusion protein product. B7.1-Fc is a dimer where each polypeptide includes the extracellular domain of human B7.1 fused to the N-terminus of the Fc portion of the human $IgG_1$ (i.e. hinge, CH2 and CH3 domain). 1B shows Coomassie blue-stained 4-20% gradient SDS-PAGE gel with lane 1 being non-reduced B7.1-Fc, lane 2 being reduced B7.1-Fc, and lane 3 being standard molecular weight markers.

The present invention provides an immunotherapeutic approach for reducing the size of a tumor or inhibiting the growth of cancer cells in an individual, or reducing or inhibiting the development of metastatic cancer in an individual suffering from cancer. Therapy is achieved by a combination of two treatments. The first is to administer a soluble form of a co-stimulatory molecule, and the second is to reduce immunoregulatory T cell activity in the individual. Immunoregulatory T cells include $CD4^+CD25^+$ T-cells.

It has been discovered that the combination of these two treatments is much more effective than either alone and achieves substantial reductions in tumor size, cancer cell growth, or reductions in metastatic cancer development in an individual suffering from cancer. Suitable co-stimulatory molecules from which the soluble co-stimulatory molecule can be derived are those expressed by antigen presenting cells. In preferred embodiments, the soluble form of the co-stimulatory molecule is derived from B7, CD137-L, CD134-L, GITR-L or CD40. More preferably, the soluble form of the co-stimulatory molecule is derived from B7.1.

The soluble form of a co-stimulatory molecule is a form of the molecule which lacks all or substantially all of the hydrophobic transmembrane domain(s) such that the molecule is rendered soluble. Thus, the soluble form of a co-stimulatory molecule is a fragment of a full length co-stimulatory molecule. For example, the soluble form of a co-stimulatory molecule includes one or more extracellular domains and optionally a cytoplasmic domain(s).

The term "co-stimulatory molecule" is used herein in accordance with its art recognized meaning in immune T cell activation. Specifically, a "co-stimulatory molecule" refers to a group of immune cell surface receptor/ligands which engage between T cells and antigen presenting cells and generate a stimulatory signal in T cells which combines with the stimulatory signal (i.e., "co-stimulation") in T cells that results from T cell receptor ("TCR") recognition of antigen on antigen presenting cells.

As used herein, a soluble form of a co-stimulatory molecule "derived from an antigen presenting cell" refers to a co-stimulatory molecule normally expressed by B cells, macrophages, monocytes, dendritic cells and other such antigen presenting cells, which has been engineered as described herein to render it soluble. Preferred soluble co-stimulatory molecules derived from an antigen presenting cell include any of B7, CD137-L, CD134-L, GITR-L and CD40. The soluble form of a co-stimulatory molecule derived from an antigen presenting cell retains the ability of the native co-stimulatory molecule to bind to its cognate receptor/ligand on T cells and stimulate T cell activation.

As used herein, "co-stimulator of T cells activation" refers to the ability of a co-stimulatory ligand to bind and to activate T cells which have been activated via TCR. Co-stimulatory activation can be measured for T cells by the production of cytokines as is well known and by proliferation assays such as are well known and described in the examples (see CFSE staining method below). The soluble form of a co-stimulatory molecule which is biologically active also may be tested for binding to the cognate receptor on activated T cells.

The soluble form of a co-stimulatory molecule derived by engineering from an antigen presenting cell may be linked to another protein which is soluble. The other protein adds additional functional capability and/or increases the serum half life of the soluble co-stimulatory molecule. For example, an immunoglobulin Fc or antibody linked to the soluble form of a co-stimulatory molecule can potentially provide antibody effector functions such as binding by Fc receptor bearing cells or activation of serum complement. The molecule size of the soluble form of a co-stimulatory molecule based on the weight of the polypeptide sequence (total polypeptide weight for the soluble form of the co-stimulatory molecule including the weight of any linked protein) generally ranges from about 60 Kd to about 260, from about 60 Kd to about 170 Kd and from about 80 Kd to about 130 Kd.

The extracellular domains (and optionally the cytoplasmic domain) of the co-stimulatory molecule may be linked to either the amino terminal or carboxy terminal end of another protein. The decision to link the soluble form of the co-stimulatory molecule to either the N or C terminus of the other protein depends on several factors, including ease of cloning and expression level. However, it is important that any choice substantially preserve the biological co-stimulatory property of the native co-stimulatory molecule. In the case of B7, the amino terminal end of the extracellular domain contains the co-stimulatory site. Thus, it can be predicted and has been determined that B7 can be attached to the amino terminal end of the other protein (e.g. if the other protein is an Fc, the fusion protein should be B7-Fc as opposed to Fc-B7). In the case of CD137-L, CD134-L, and GITR-L, attachment is preferably to the carboxy terminal end of the other protein (e.g., Fc-CD137-L as opposed to CD137-L-FC). However, attachment to the amino terminal end may be possible if activity is preserved. The same principles also apply to linkage to large proteins such an antibody. For example, B7 can be attached to the amino terminal end of the heavy chain of an antibody and CD137-L can be attached to the carboxy end of the heavy chain (at the constant region).

In one embodiment, the soluble form of the co-stimulatory molecule is administered fused to the Fc of an immunoglobulin such as an Fc from IgG or to an antibody that targets a cancer cell. Such immunoglobulin Fc is preferably a human Ig Fc.

The reconstructed sequence can be inserted into a suitable expression system such as Glutamine Synthesis Gene Amplification System using expression vector pEE12 and transfected into the NSO murine myeloma cell line. The expressed fusion protein can be purified by tandem protein-A affinity and ion-exchange chromatography. By fusing IgG Fc to the C-terminus of the extracellular domain of a co-stimulatory molecule such as a B7 molecule, the soluble form of the co-stimulatory molecule is expressed as a dimeric nonaggregated molecule.

Soluble co-stimulatory molecules prepared as described herein can bind to T cells and stimulate their proliferation. The immunotherapeutic anti-tumor effect of such soluble co-stimulatory molecules when combined with a reduction in immunoregulatory T cell activity is believed to be mediated by $CD8^+$ cells. For example, it has been found that the anti-cancer effect of the B7.1-Fc co-stimulator fusion protein combined with a treatment for reducing immunoregulatory T cell activity in an individual with cancer is much greater than if either treatment is used alone. Reduction in immunoregulatory T cell activity is preferably achieved by administering an antibody that depletes $CD4^+$ or $CD25^+$ T-cell subsets.

As used herein, the term "B7" refers to B7.1 (CD80), B7.2 (CD86) or any other B7 molecule that has biological function as co-stimulatory molecules as ligands for CD28 and CTLA-4, and that shares at least 80% amino acid sequence identity, preferably at least 90% sequence identity, more preferably at least 95% sequence identity and even more preferably at least 98% sequence identity with the sequence of human B7.1 or B7.2. The amino acid sequence and encoding nucleotide sequence of B7 family members are known and publicly available.

The sequence of human B7.1 (CD80) also referred to as "CD28 antigen ligand" contains 288 amino acids of which 34 amino acids at the N terminus represent the signal sequence (see sequence in Swiss Prot Id no. P33681). A transmembrane domain is located at resides 243-263 and the cytoplasmic domain is located at residues 264-288. The nucleotide sequence of human B7.1 (2824 bp) is available in public databases (see Genbank accession no. NM_005191). B7.1 is described by Fields et al. 1998.

The sequence of human B7.2 (CD86) is represented by two isoforms. The main isoform contains 329 amino acids of which 23 amino acids at the N terminus represent the signal sequence (see sequence in Swiss Prot Id no. P42081). A transmembrane domain is located at resides 248-268 and the cytoplasmic domain is located at residues 269-329. The nucleotide sequence of human B7.2 (1424 bp) is available in public databases (see Genbank accession no. U04343). B7.2 is described by Yamaguchi et al. 2004.

As used herein, the term "CD137" (a.k.a. 4-1 BB ligand receptor) refers to a specific molecule associated with this name and any other molecules that have biological function as co-stimulatory molecules that share at least 80% amino acid sequence identity, preferably at least 90% sequence identity, more preferably at least 95% sequence identity and even more preferably at least 98% sequence identity with human CD137 as defined in Swiss Prot Id. no. Q07011).

The sequence of human CD137 contains 255 amino acids of which 23 amino acids at the N terminus represent the signal sequence (see sequence in Swiss Prot Id no. Q07011). A transmembrane domain is located at resides 187-213 and the cytoplasmic domain is located at residues 214-255. The nucleotide sequence of CD137 (1645 bp) is available in public databases (see Genbank accession no. NM_003811). CD137 is described by Seko et al. J Vasc Res 41 (1), 84-90 (2004). CD137 is expressed almost exclusively on TCR activated T cells.

As used herein, the term "CD137-L" (a.k.a. 4-1 BB ligand or TNFL9) refers to a specific molecule associated with this name and any other molecules that have biological function as co-stimulatory molecules that share at least 80% amino acid sequence identity, preferably at least 90% sequence identity, more preferably at least 95% sequence identity and even more preferably at least 98% sequence identity with human CD137-L as defined in Swiss Prot Id. no. P41273).

Human CD137-L is a type II membrane protein that contains 254 amino acids (no signal sequence) (see sequence in Swiss Prot Id no. P41273). The protein contains a cytoplasmic domain at residues 1-28, a transmembrane domain at resides 29-49 and an extracellular domain at residues 50-254. The nucleotide sequence of CD137-L (1645 bp) is available in public databases (see Genbank accession no. NM_003811). CD137-L is described by Alderson et al. *Eur J. Immunol.* 1994 September; 24(9):2219-27. CD137-L is expressed on antigen presenting cells including B cells, monocytes, and splenic dendritic cells and T lymphocytes. CD137-L interacts with CD137 on activated T cells.

As used herein, the term glucocorticoid-induced tumor necrosis factor receptor "GITR" ligand (a.k.a. GITR-L, TNFSF18 (tumor necrosis factor (ligand) superfamily, member 18)) refers to a specific molecule associated with this name and any other molecules that have biological function as co-stimulatory molecules that share at least 80% amino acid sequence identity, preferably at least 90% sequence identity, more preferably at least 95% sequence identity and even more preferably at least 98% sequence identity with GITR-L as defined in Swiss Prot Id. no. Q9UNG2).

Human GITR-L is a type II membrane protein that contains 177 amino acids (no signal sequence) (see sequence in Swiss Prot Id no. Q9UNG2). The protein contains a cytoplasmic domain at residues 1-28, a transmembrane domain at resides 29-49 and an extracellular domain at residues 50-177. The nucleotide sequence of GITR-L (610 by of which 21. to 554 encode the protein) is available in public databases (see Genbank accession no. NM_005092.2). GITR-L is described by Kim et al. Invest. Opthalmol. Vis. Sci. 45 (9), 3170-3176 (2004). GITR-L binds to GITR present on the surface of antigen presenting cells. Expression of the GITR-L is restricted to immature and mature splenic dendritic cells. This cytokine is a ligand for receptor TNFRSF18/GITR which is a member of the TNF receptor family and is expressed preferentially at high levels on CD25+CD4+ regulatory T cells. This cytokine is also found to be expressed in endothelial cells, and is thought to be important for interaction between T lymphocytes and endothelial cells.

As used herein, the term "CD134-L (a.k.a. OX40 ligand or TNRSF4) refers to a specific molecule associated with this name and any other molecules that have biological function as co-stimulatory molecules that share at least 80% amino acid sequence identity, preferably at least 90% sequence identity, more preferably at least 95% sequence identity and even more preferably at least 98% sequence identity with CD134-L as defined in Swiss Prot Id. no. P23510).

Human CD134-L is a type II membrane protein which contains 183 amino acids (no signal sequence). The protein contains a cytoplasmic domain at residues 1-23, a transmembrane domain at residues 24-50 and an extracellular domain at residues 51-183. The nucleotide sequence of CD134-L (3510 bp, with the coding sequence being 157-708) is available in public databases (see Genbank accession no. NM_003326.2). CD134-L is described by Godfry et al., J Exp Med. 1994 Aug. 1; 180(2):757-62. CD134-L is expressed by dendritic cells and other APC and binds to CD134 which is present on activated T cells.

As used herein, the term "CD40" (a.k.a. TNFRSF5 or CD40 ligand receptor) refers to a specific molecule associated with this name and any other molecules that have biological function as co-stimulatory molecules that share at least 80% amino acid sequence identity, preferably at least 90% sequence identity, more preferably at least 95% sequence identity and even more preferably at least 98% sequence identity with CD40 as defined in Swiss Prot Id. no. P25942).

The sequence of human CD40 contains 277 amino acids of which 20 amino acids at the N terminus represent the signal sequence (see sequence in Swiss Prot Id no. P25942). A transmembrane domain is located at resides 194-215 and the cytoplasmic domain is located at residues 216-277. The nucleotide sequence of CD40 (1177 bp) is available in public databases (see Genbank accession no. NM_001250). CD40 and various isoforms are described by Tone et al. Proc. Natl. Acad. Sci. U.S.A. 98 (4), 1751-1756 (2001). CD40 is expressed by monocytes and B cells binds to CD40-L (a.k.a. CD40 ligand or CD153) expressed by activated T cells.

As used herein the reference to a "soluble form" of a co-stimulatory molecule which includes B7, CD137-L, CD134-L, GITR-L or CD40 refers to any form of the molecule that retains co-stimulatory activity but lacks a transmembrane domain. For example, a soluble form of B7 is the extracellular domain of B7. A soluble form of the co-stimulatory molecule also may be a fragment of the extracellular domain(s). A soluble form of a co-stimulatory molecule also may include the cytoplasmic domain or other domain provided that it does not render the molecule insoluble.

Cancers treatable using the methods of the invention include carcinomas, sarcomas, and leukemias and lymphomas and other types of cancer. Carcinomas include those of lung, breast, colon, ovarian, prostate, and the like. These cancers may be primary or metastatic. In the case of leukemias and lymphomas, the cancer cells treatable with the invention methods include those in the form of a solid tumor as well as cancer cells in the bone marrow and in the circulation.

The term "antibody" as used herein includes immunoglobulins, which are the product of B cells and variants thereof as well as the T cell receptor (TcR), which is the product of T cells, and variants thereof. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass.

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the F(ab')2 dimer into an Fab' monomer. The Fab' monomer is essentially a Fab fragment with the hinge region (see, Fundamental Immunology, W. E. Paul, ed., Raven Press, N.Y. (1993), for a more detailed description of other antibody fragments). A Fab fragment and Fc fragment are generated by digesting IgG with papain. Papain cleaves in the hinge region just above the residues involved in interchain S—S bonding, resulting in monovalent Fab fragments and the Fc fragment, which includes two constant region fragments, each containing the lower part of the hinge, CH2 and CH3 domains. The constant region fragments of the Fc are stabilized as a dimer though interchain S—S bonding of the lower residues of the hinge region.

Immunoglobulin "Fc" classically refers to the portion of the constant region generated by digestion with papain. Includes the lower hinge which has the interchain S—S bonds. The term "Fc" as used herein refers to a dimeric protein comprising a pair of immunoglobulin constant region polypeptides, each containing the lower part of the hinge, CH2 and CH3 domain. Such "Fc" fragment may or may not contain S—S interchain bridging in the hinge region. It should be understood that an Fc may be from any Ig class and, as such, may include a CH4 domain such as in the case of IgM. Mutant sequences of an Fc are known such as described by Wines et al., *J. Immunol.* 2000 May 15; 164(10):5313-8 and may be used herein.

While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

Recombinant antibodies may be conventional full length antibodies, antibody fragments known from proteolytic digestion, unique antibody fragments such as Fv or single chain Fv (scFv), domain deleted antibodies, and the like. Fragments may include domains or polypeptides with as little as one or a few amino acid deleted or mutated while more extensive deletion is possible such as deletion of one or more domains.

An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See e.g., Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513, 5,132,405 and 4,956,778.

An antibody may be a non-human antibody, a human antibody, a humanized antibody or a chimeric antibody, the latter comprising human and non-human antibody sequence. As is known in the art, chimeric antibody is prepared by exchanging a non-human constant region (heavy chain, light chain or both) with a human constant region antibody. See e.g. U.S. Pat. No. 4,816,567 to Cabilly et al. Methods of making humanized antibodies from non-human antibodies such as from murine antibodies are also well known (see, e.g., U.S. Pat. No. 5,565,332 to Winter).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted, e.g., by the local homology algorithm of Smith and Waterman (1981, Adv. Appl. Math. 2:482) by the homology alignment algorithm of Needleman and Wunsch, (1970, J. Mol. Biol. 48:443) by the search for similarity method of Person and Lipman (1988, Proc. Nat'l. Acad. Sci. USA 85:2444) by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. For example, a substantial portion of the human genome sequence is available for searching via the BLAST search tool at the National Center for Biotechnology Information (NCBI). Information about multiple sequenced genomes and the resources to analyze them also is available from NCBI on its Genomic Biology web page.

One example of a useful algorithm is BLAST (e.g., BLAST 2.0), which is described in Altschul et al., 1977, Nucl. Acids Res. 25:3389-3402, and Altschul et al., J. Mol. Biol., 1990 215:403-410, respectively. Software for performing BLAST analyses is publicly available through the National Center for Biotechnology Information. This algorithm involves first identifying high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., supra, 1977 and 1990). These initial neighborhood word hits act as seeds for initiating searches to find longer HSPS containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment.

The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectations (E) of 10, and the BLOSUM62 scoring matrix (see Henikoff and Henikoff, Proc. Natl. Acad. Sci. USA (1989) 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, 1993, Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

The soluble form of the co-stimulatory molecule may be linked to another protein or polypeptide. Such other polypeptide may be the Fc portion of an immunoglobulin, albumin, or any other type of serum protein or fragment thereof which maintains the solubility of the co-stimulatory molecule. The soluble form of the co-stimulatory molecule may be linked to an immunoglobulin via the heavy and/or light chain, which may be a fragment or a full length heavy or light chain. The immunoglobulin may be an antibody that can target an antigen associated with a cancer cell or tumor.

The soluble form of the co-stimulatory molecule may be linked to antibody which is targets cancer cells or tumors in vivo. In one embodiment, the antibody is specific for a tumor cell-surface antigen. In another embodiment, the antibody is specific for a stromal component of a tumor. In yet another embodiment, the antibody is specific for an intracellular antigen, such as an intranuclear antigen(s). In the latter case, the antibody may be a humanized or human chimeric antibody based on the murine antibody TNT-1, TNT-2, TNT-3. The human antibody NHS76 is a genetically engineered counterpart to TNT-1.

TNT antibodies bind intracellular antigens found in all cells and which are retained by dying cells and which show preferential localization in malignant tumors due to the presence of abnormally permeable, degenerating cells only rarely present in normal tissues. Rapidly dividing tumors contain a proportion of degenerating or dead cells, but, with attention focused upon attempts to kill the dividing cells, the degenerating component has largely been ignored. Calculations of tumor cell loss have revealed that, in contrast to normal tissues, 30-80% of the progeny of tumor cell divisions shortly undergo degeneration. In tumors, the imperfect vasculature and impaired phagocytic response, permit the accumulation of degenerating cells, often with the formation of large areas of necrosis, long recognized by pathologists to be a typical feature of malignant tumors (Epstein, et al., *Cancer Res* (1988) 48:5842-5848). Thus, the accumulation within tumors of a high proportion of dying cells constitutes a major distinction between malignant tumors and normal tissues wherein sporadic cell death occurs at a relatively low rate and is accompanied by a rapid (within minutes) and orderly removal of necrotic elements from the tissue. Since degenerating cells have a permeable cell surface membrane not observed in viable cells, TNT antibodies enter and bind to their intracellular antigens in necrotic areas of the tumor. Contrarily, TNT antibodies diffusing in viable regions of the tumor and normal tissues do not bind and are removed from the circulation by normal clearance mechanisms. Hence, TNT antibodies provide a useful approach for specifically targeting necrotic regions of tumors and can be used to deliver diagnostic and therapeutic reagents into these regions which are may be situated deep within the central core of tumors.

TNT antibodies have a number of unique features that distinguishes from other forms of antibody therapy.

The sequence of TNT antibody NHS76 can be found in U.S. Pat. No. 6,827,925.

As used herein, "linked" means that under physiological conditions of pH, ionic strength and osmotic potential, the majority of the entities are associated with each other at equilibrium. Covalent linkage may be by any of a variety of chemical crosslinking agents including, for example, homobifunctional or heterobifunctional crosslinking reagents, many of which are commercially available (see, e.g., Pierce Chemical Co. or Sigma Chemical Co.). Crosslinking can be achieved by any of a variety of chemistries well known in the art including, for example, activated polyethylene glycols, aldehydes, isocyanates, maleimides and the like.

The soluble form of a co-stimulatory molecule may be linked to another protein by genetic fusion and may include a polypeptide linker sequence between the two entities. The composition and length of the linker may be determined in accordance with methods well known in the art and may be tested for efficacy. The linker is generally from about 3 to about 15 amino acids long, more preferably about 5 to about 10 amino acids long, however, longer or shorter linkers may be used or the linker may be dispensed with entirely. A Gly$_4$Ser linker is an exemplary linker. Additional sequences may also be included to incorporate a cleavage site to separate the soluble form of the co-stimulatory molecule and the immunoglobulin Fc or other polypeptide at some later time. Thus, the linker may include a sequence that is a substrate for enzyme cleavage, e.g., an endopeptidase recognition sequence.

The soluble form of a co-stimulatory molecule (including fusion proteins thereof) and agents that can remove, deplete or inhibit the activity of immunoregulatory T cells may be prepared using recombinant expression methods such as in prokaryotic or eukaryotic cells as is well known in the art. (see e.g., U.S. Pat. Nos. 5,116,943 and 6,331,415). In general, nucleic acid encoding the protein can be cloned into an expression vector for high yield expression of the encoded product. The expression vector can be part of a plasmid, virus, or may be a nucleic acid fragment. The expression vector includes an expression cassette into which the nucleic acid encoding the protein is cloned in operable association with a promoter and optionally an enhancer. The expression cassette may also include other features such as an origin of replication, and/or chromosome integration elements such as retroviral LTRs, or adeno associated viral (AAV) ITRs. If secretion of the protein is desired, DNA encoding a signal sequence may be placed upstream of the nucleic acid encoding the mature amino acids of the protein. DNA encoding a short protein sequence that could be used to facilitate later purification (e.g., a histidine tag) or assist in labeling the protein may be included within or at the ends of the protein encoding nucleic acid.

The soluble form of the co-stimulatory molecule may be fused from its N-terminus or C-terminus directly or indirectly to the C-terminus or N-terminus of another polypeptide (e.g., a hinge-CH2—CH3 of an Ig Fc). In some cases, the soluble form of the co-stimulatory molecule is preferably fused at its C-terminus to the N-terminus of the other polypeptide.

Cells suitable for replicating and for supporting recombinant expression of protein are well known in the art. Such cells may be transfected or transduced as appropriate with the particular expression vector and large quantities of vector containing cells can be grown for seeding large scale fermenters to obtain sufficient quantities of the protein for clinical applications. Such cells may include prokaryotic microorganisms, such as *E. coli*, or various other eukaryotic cells, such as Chinese hamster ovary cells (CHO), insect cells, or the like. Standard technologies are known in the art to express foreign genes in these systems.

Reducing the activity of immunoregulatory T cells in an individual as part of the methods of the invention may be achieved by removing ex vivo or by depleting or inactivating immunoregulatory T cells in the individual. The term "immunoregulatory T cells" as used herein refers to a population of T cells that function, directly or indirectly, to suppress the host anti-tumor immune response. Immunoregulatory T cells may be CD4+, CD25+ or positive for both markers.

The term "removing ex vivo" as used herein with reference to immunoregulatory T cells means that immunoregulatory T cells are removed from the circulation of an individual by an ex vivo method such as flow cytometric cell separation, column or filter separation, and the like. The column or filter may have bound thereto an antibody that can bind to immunoregulatory T cells. Antibodies that bind to immunoregulatory T cells also may be used to identify such cells for removal by a flow cytometric device. Antibody suitable for binding to immunoregulatory T cells include antibody specific for the CD4 antigen, the alpha chain subunit of the IL-2 receptor (i.e. CD25), and the like. A combination of such anti-T cell antibodies also may be used. Daclizumab®, a humanized monoclonal antibody that binds to CD25 or Basiliximab®, a chimeric version of this same antibody is commercially available from Novartis Pharma AG. Hu-Max-CD4®, a fully humanized antibody against CD4 has been made (GenMab). CD4 antibody is described by North and Awwad 1990, while CD25 is described by Onizuka et al. 1999.

The term "depleting or inactivating in vivo immunoregulatory T cells" as used herein refers to a reduction in the number or functional capability of immunoregulatory T cells which suppress the host anti-tumor immune response that occurs following administration of a pharmaceutical agent to the host. The pharmaceutical agent is one that when administered causes a loss of immunoregulatory T cells (i.e., depletion) or inactivation of anti-tumor immune suppression function of the immunoregulatory T cells. The ultimate result of such treatment is to reduce immunoregulatory T cell activity in the recipient of the treatment.

Depleting or inactivating immunoregulatory T cells may be achieved by administering a pharmaceutical agent such as an antibody specific for the CD4 antigen, the alpha chain subunit of the IL-2 receptor (i.e. CD25), and the like, as described above. Also, an antibody to gamma delta immunoregulatory T cells can be used to deplete such cells and stimulate anti-tumor immunity as described previously. Seo et al., J. Immunol. (1999) 163:242-249. Anti-CD40 ligand, also may be used to deplete or inactivate immunoregulatory T cells.

Partial antibody constructs such as CTLA4Ig, a fusion protein of CTLA-4 and Fc of immunoglobulin (Ig) heavy chain, can be used to inhibit the essential co stimulatory signal for full T cell activation via blocking the interaction between CD28 and B7 molecules. CTLA4Ig may be administered as a pharmaceutical to render regulatory T cells nonresponsive (i.e. inactivation). See Park et al. Pharm Res. (2003) 20(8):1239-48. An IL-2 fusion to pseudomonas exotoxin (OnTac) is yet another agent for depleting or inactivating regulatory T cells.

In another approach, agents may be administered that prevent the induction of CD8+ cytolytic T-lymphocyte (CTL) tumor anergy. Agents that agonize CD137, such as agonistic antibodies, may be used to restore the tumor cytolytic function of established anergic CTLs upon reencountering their cognate antigen. See Wilcox et al., Blood (2004) 103:177-184. This approach can be used to break T-cell tolerance to tumor antigens.

Agents that agonize glucocorticoid-induced tumor necrosis factor receptor (GITR) ligand on CD4/CD25+ immunoregulatory T cells reverses the suppressive action of these cells. GITR ligand agonists are described in Tone et al., PNAS (2003) 100:15059-15064; Stephens et al. 2004 and Shimizu et al. 2002).

Antibodies to neurophilin (e.g. Bruder et al. 2004) and antibodies to CTLA-4 (e.g. Leach et al. 1996) also can be administered in vivo to deplete immunoregulatory T cells or reduce their activity.

Methods of removing, depleting or inactivating immunoregulatory T cells may be used even if the methods are not limited solely to such cells. Effort to remove, deplete or inactivate immunoregulatory T cells may be performed multiple times during a given period of treatment. Also, different methods may be used together (e.g., ex vivo cell removal and in vivo depletion or inactivation). The amount of anti-T cell antibody administered for depletion or inactivation may be similar to the amount used in the transplantation field. See, e.g., Meiser et al., Transplantation. (1994) 27; 58(4): 419-23.

Immunoregulatory T cells may be removed, depleted or inactivated before, during and/or after administration of the soluble form of the co-stimulatory molecule. Immunoregulatory T cells are preferably removed, depleted or inactivated before administering the soluble form of the co-stimulatory molecule.

In a further embodiment, the invention methods for cancer therapy may include adoptive transfer of immune cells to enhance anti-tumor immunity. As used herein "adoptive transfer" refers to the administration of immune cells, from another individual or from the same individual. These are preferably T cells, which may be activated ex vivo to enhance their ability to function in supporting an anti-tumor immune response. Adoptively transferred immune cells may be activated ex vivo by any of a variety of well known agents including, for example, exposure to IL-2 and/or to anti-CD3 antibodies. Ex vivo activation also may include exposure to a cancer cell vaccine. Such cancer cell vaccine may constitute live (but non-replicating), or killed cancer cells from the individual to be treated or from another cancer entirely. The vaccine also may be a cancer cell extract or purified vaccine preparation derived from cancer cells. Cancer cell vaccines are well known in the art and may be prepared in accordance with well known methods.

In this form of therapy, patients receive multiple infusions of T-cells after ex vivo stimulation with IL-2 (Lum, et al., J. Immunother. (2001) 24:408-19) or other agents such as anti-CD3+ and anti-CD28+ antibodies (June, C. H.: J. Immunother (2001) 24(5): 389-391).

Compounds described herein can be administered as a pharmaceutical or medicament formulated with a pharmaceutically acceptable carrier. Accordingly, the compounds may be used in the manufacture of a medicament or pharmaceutical composition. Pharmaceutical compositions of the invention may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. For rectal administration, the invention compounds may be combined with excipients such as cocoa butter, glycerin, gelatin or polyethylene glycols and molded into a suppository.

Compounds may be formulated to include other medically useful drugs or biological agents. The compounds also may be administered in conjunction with the administration of other drugs or biological agents useful for the disease or condition to which the invention compounds are directed.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. Dosage levels typically fall in the range of about 0.001 up to 100 mg/kg/day; with levels in the range of about 0.05 up to 10 mg/kg/day are generally applicable. A compound can be administered parenterally, such as intravascularly, intravenously, intraarterially, intramuscularly, subcutaneously, or the like. Administration can also be orally, nasally, rectally, transdermally or inhalationally via an aerosol. The compound may be administered as a bolus, or slowly infused.

A therapeutically effective dose can be estimated initially from cell culture assays by determining an IC50. A dose can then be formulated in animal models to achieve a circulating plasma concentration range that includes the IC50 as determined in cell culture. Such information can be used to more accurately determine useful initial doses in humans. Levels of drug in plasma may be measured, for example, by HPLC. The exact formulation, route of administration and dosage can be chosen by the individual physician in view of the patient's condition.

The administration of soluble co-stimulatory molecules or other proteins described herein to an immunocompetent individual may result in the production of antibodies against the soluble co-stimulatory molecules or other proteins. Reducing the immunogenicity of the soluble co-stimulatory molecules or other proteins can be addressed by methods well known in the art such as by attaching long chain polyethylene glycol (PEG)-based spacers, and the like, to the agent. Long chain PEG and other polymers are known for their ability to mask foreign epitopes, resulting in the reduced immunogenicity of therapeutic proteins that display foreign epitopes (Katre et al., J. Immunol. (1990,) 144, 209-213; Francis et al., Int. J. Hematol. (1998) 68, 1-18). Alternatively, or in addition, the individual administered the cancer therapeutic agents or compositions may be administered an immunosuppressent such as cyclosporin A, anti-CD3 antibody, and the like.

The following examples serve to illustrate the present invention. These examples are in no way intended to limit the scope of the invention.

EXAMPLES

Experiments using human B7.1 or B7.2 fused to an IgG Fc or to an anti-TNT antibody were evaluated for tumor therapy in mice. Human B7.1 and B7.2 is able interact functionally with the murine counter-receptors CD28 and CTLA-4 (Gerstmayer, et al., *Cancer Immunol. Immunother.* 45: 156-158), allowing the anti-tumor efficacy of B7.1-Fc, B7.2-Fc and B7.1/NHS76 to be tested in murine tumor models such as Colon 26, RENCA, and MAD109 tumors implanted in BALB/c mice. NHS76 is a human TNT antibody, which targets human solid tumors by binding to intracellular antigens exposed in degenerating cells associated with tumor necrosis (Epstein 1988, *Cancer Res.* 48:5842-5848; Sharifi et al., 2001).

Example 1

Materials and Methods

Reagents and Mice

The Glutamine Synthetase Gene Amplification System, including the expression plasmid pEE12, was obtained from Lonza Biologics (Slough, U. K.). The plasimid pBJ, containing human B7.1 (huB7.1) cDNA (nucleotide sequence identical to GenBank accession number M27533), was obtained from the American Type Culture Collection (Manassas, Va.). Restriction endonucleases, T4 DNA ligase, Vent polymerase, and other molecular biology reagents were obtained from either New England Biolabs (Beverly, Mass.) or Boehringer Mannheim (Indianapolis, Ind.). Chloramine T, GSEM (50×), and 2,2'-azino-bis(3-ethylbenzthiazoline-6-sulfonic acid) diammonium salt (ABTS) were obtained from Sigma Chemical Co. (St. Louis, Mo.). Characterized and dialyzed fetal calf sera (FCS) were obtained from Hyclone Corp. (Logan, Utah), and RPMI 640 medium, Selective Hybridoma Medium (SFM) without L-glutamine, MEM non-essential amino acids solution (100×), and phosphate-buffered saline (PBS) were obtained from GIBCO LifeTechnologies, Inc. (San Diego, Calif.). Sulfosuccinimidyl 6-(iotinamido) hexanoate (Sulfo-NHS-LC biotin) was obtained from Pierce (Rockford, Ill.). Horseradish peroxidase (HRPO)-conjugated secondary reagents (goat-antihuman immunoglobulin G [IgG; FcSp] and streptavidin) were obtained from CalTag (Burlingame, Calif.).

Six-week-old female BALB/c mice were obtained from Harlan Sprague Dawley (Indianapolis, Ind.). Institutional Animal Care and Use Committee (IACUC) approved protocols and institutional guidelines for the proper and humane use of animals in research were followed.

Antibodies and Tumor Cell Lines

Biotin-anti-CD4 (RM4-4 clone), Biotin-anti-CD8 (2.43 clone) FITC-anti CD4 (RM4-4 clone), PE-anti CD25 (7D4 clone), PE-anti CD8a mAb and HRP-streptavidin were purchased from BD Pharmingen (San Diego, Calif.). Hybridomas, including rat antimouse L3T4 (anti-CD4) mAb GK1.5, anti-lyt (anti-CD8) mAb 2.43, anti CD8β (H35), and anti-IL-2 receptor (anti-CD25) mAb 7D4 and PC61 were obtained from the American Type Culture Collection. To obtain sufficient quantities of reagents, hybridoma cells were grown in Integra CL 1000 Culture Chambers (IBS Integra Biosciences, Wallisellen, Switzerland) and purified by tandom Protein-A affinity chromatography and Q-Sepharose ion-exchange chromatography (Bio-Rad Laboratories, Hercules, Calif.). Horseradish peroxidase (HRP)-conjugated goat-anti-human IgG (Fc specific) and the activating antibodies, purified rat-anti-mouse CD3 (17A2) and rat-anti-mouse CD28 were obtained from Caltag (Burlingame, Calif.).

The NS0 murine myeloma cell line was obtained form Lonza Biologics. The Colon 26 murine colorectal adenocarcinoma and the RENCA murine renal carcinoma were obtained from the American Type Culture Collection. The Mad 109 murine lung carcinoma cell line was obtained from the National Cancer Institute (Frederick, Md.). All three murine tumor cell lines were originally derived from BALB/c mice.

Construction of B7-Fc Fusion Protein

An expression plasmid was constructed containing sequence encoding a fusion protein that included from the 5' end, DNA encoding human B7.1 signal and extracellular domains (B7.1 sig/ex) and 3' to that, DNA encoding the hinge/CH2/CH3 domain of human $IgG_1$ (the latter can be referred to as an Fc since it will dimerize as a native Fc when expressed). cDNA encoding the signal and extracellular domains of human B7.1 was generated by PCR amplification from the encoding cDNA (ATCC source). The amplified segment of the cDNA extends from the sequence encoding the initiation Met in the signal sequence through that encoding $Asp^{241}$.

A cDNA (Fragment 1) encoding B7.1 sig/ex was obtained by primary PCR of B7.1 cDNA with primers 5'-TTC TCT AGA ATG GGC CAC ACA CGG-3'(FWD1) and 5'-TGTGT-GAGTTTTGTCATCAGGAAAATGCTCT TGCTT-3' (BWD1). The primer FWD1 includes an XbaI restriction site at the 5' end and primer BWD1 includes a portion of hinge region complementary sequence at the 3' end. The human Fc cDNA (Fragment 2) encoding the hinge-CH2-CH3 portion of human IgG1 was PCR amplified with primers 5'-GAG CAT TTT CCT GAT GAC AAA ACT CAC ACA TGC CCA-3' (FWD2) and 5'-TGA TTA ATG ATC AAT GAA TTC TCA TTT ACC CGG AGA CAG GGA-3'(BWD2). The primer FWD2 includes a portion of the B7.1 sig/ex 3' sequence at the 5' end and primer BWD2 contains EcoR1 and Bcl1 restriction sites at the 3' end. The B7.1-Fc fusion DNA was produced by assembling Fragment 1 and Fragment 2 using primers FWD1 and BWD2.

A PCR product containing the B7.1-Fc gene (encoding huB7.1 sig/ex-hinge/CH2/CH3) was obtained with 5' and 3' DNA containing XbaI and EcoR1 cloning sites, respectively. The huB7.1 sig/ex-hinge/CH2/CH3 encoded polypeptide when expressed by cells results in removal of the signal sequence. The resulting polypeptides form dimers via the hinge/CH2/CH3 portion of the fusion. The dimerized polypeptide can thus be viewed as a B7.1 ex-Fc fusion protein (also referred to herein as "B7.1-Fc").

The fusion expression gene was produced by single-step insertion of the BT1-Fc gene into an XbaI and EcoRI site in pEE12 expression vector. Thus, B7.1-Fc gene encoding huB7.1 sig/ex-hinge/CH2/CH3 and with 5' XbaI and 3' EcoR1 cloning sites was digested with XbaI and EcoR1 and cloned into the pEE12 expression vector similarly digested. The resulting expression vector is referred to as pEE12/huB7.1-Fc.

An expression vector encoding human huB7.2 sig/ex-hinge/CH2/CH3 was prepared similarly as for B7.1.

Expression and Purification of B7.1-Fc

B7.1-Fc and B7.2-Fc fusion proteins were expressed in NS0 murine myeloma cells for long-term stable expression according to the manufacturer's protocol (Lonza Biologics). The highest producing clones were scaled up for incubation in an 8-L stir flask bioreactor using 5% heat-inactivated dialyzed fetal calf serum and the fusion protein purified from the spent culture medium by sequential Protein A affinity chromatography and ion-exchange chromatography. Heat-inactivated (68° C. for 1 h) dialyzed fetal calf serum was used to prevent the induction of endogenous proteolytic enzymes and the subsequent cleavage of the fusion protein produced in the NS0 cells. The fusion protein was analyzed by sodium dodecyl sulfate-polyacrylamide gel electrophoresis (SDS-PAGE) under reducing conditions and stained with Coomassie Blue to demonstrate proper assembly and purity.

T-Lymphocyte Proliferation Assay

Peripheral blood was collected from healthy donors and mononuclear lymphocytes (PBMC) were isolated with gradient centrifugation. Five×$10^4$/well PBMC were cultured in 96-well plates pre-coated with 0.4 ug/ml anti-CD3 mAb and 5 ug/ml B7.1-Fc. After a 3 day incubation, T-cell proliferation was measured by cell counting and MTS One Solution Kit (Promega Corp.).

Depletion of Lymphocyte Subsets In Vivo

Antibodies were administrated 1 day before tumor implantation and every 5-7 days thereafter for the T-cell depletion studies. For $CD4^+$, $CD8^+$, and $CD25^+$ T-cell depletion, 0.5 mg of anti-CD4 (GK1.5), anti-CD8 (2.43), or anti-CD25 (PC61) were injected i.p. in a 1 ml inoculum. Depletion of specific T-cell subsets was confirmed by flow cytometric analysis of splenocytes from treated mice. Each of these studies was repeated two or three times, and each group contained 5 mice per group.

Immunotherapy Studies

Groups (n=5) of 6-week old female BALB/c mice were injected s.c. in the left flank with a 0.2 ml inoculum containing 5×$10^6$ Colon 26, RENCA, or MAD 109 cells under a University Animal Care Committee approved protocol. Treatments were started when tumors reached ~0.5 cm in diameter. Groups of tumor-bearing mice (with or without lymphocyte subset depletion) were treated i.v. with a 0.1 ml inoculum containing B7.1-Fc (20 µg) or control isotype matched antibody (20 µg). All the groups were treated daily times 5, and tumor growth was monitored every other day by caliper measurement in three dimensions. Tumor volumes were calculated by the formula: length×width×height. The results were expressed as the mean±SD, and the significance levels (P value) were determined using the Wilcoxon rank-sum test. Each of these studies was repeated twice.

Rechallenge Experiments

Two months after the completion of the initial immunotherapy, tumor-free mice successfully treated and control naïve mice (n=5) were challenged with $10^6$ Colon 26 and MAD109 cells or Colon 26 and RENCA cells in the left and right flanks, respectively. The injection sites were observed for 2 months. Tumor volumes were measured every week and calculated as described before. To study the presence of $CD4^+$ $CD25^+$ T-cells in different groups, tumor draining lymph nodes (TDLN) were removed, and T-reg cells were stained with PE-anti-CD25 and FITC-anti-CD4 for FACS analysis.

Analysis of Lymphocytes in Tumors of Treated Animals.

Tumors from control and treated mice were aseptically removed on days 14 and 21 after tumor implantation, and manually cut into 1 $mm^3$ pieces in a sterile Petri dish. The small tissue fragments were then digested with 0.01% Hyaluranidase and 0.1% Collagenase (Sigma Chemical Co.) in RPMI 1640 for 3 hours at 37° C. with continuous stirring. The resulting single cell suspensions were then washed twice with 0.1% FCS in PBS and stained by standard flow cytometry methods. To detect subpopulations of lymphocytes infiltration in tumors, the following conjugated antibodies were used for FACS: PE-anti-CD8, FITC-anti-CD4, PE-anti-CD25, APC-anti-CD11b, FITC-anti-CD11c, and PE-anti-Pan NK (BD Bioscience PharMingen, San Diego, Calif.).

Intracellular IFN-γ and IL-2 Production.

TDLNs from control and treated mice were removed on day 14 and 21 after tumor implantation. Single cell suspensions were obtained and 2×$10^6$ viable cells/well were plated into a 24-well plate. Intracellular IFN-γ and IL-2 production were performed as follows. Briefly, cells were stimulated for 24 hours in complete RPMI 1640 containing 10 ng/ml PMA (Sigma, Aldrich) and 1 µg/ml ionomycin (Sigma). The cells were transferred into anti-mouse CD3e precoated wells in the presence of 2 µg/ml anti-mouse CD28 antibody and GolgiStop (BD PharMingen). Cells were then washed and mouse Fc receptors were blocked with 1 µg Fc blocking antibody (CD16/CD32) per $10^6$ cells in 100 µl staining buffer (1% FBS in PBS) for 15 minutes at 4° C. Cells were then stained with a PE-conjugated anti-CD3e antibody for 30 min at 4° C., fixed and permeabilized with 100 µl Cytofix/Cytoperm (BD PharMingen) for 15 min at 4° C., and washed with 300 µl of Perm/Wash (BD PharMingen). The fixed cells were then resuspended in 100 µl Perm/Wash buffer containing of FITC-anti-IFN-γ or FITC-anti-IL-2 antibody (BD PharMingen) for 30 min at 4° C. in the dark. Cells were washed and resuspended in FACS buffer and the intracellular production of IFN-γ or IL-2 were analyzed by FACS.

T-Cell Proliferation Assay.

The proliferation of T-cells was measured by CFSE vital staining. CFSE is a dye that spontaneously and irreversibly binds to intracellular proteins. On cell division the CFSE labeling is equally distributed among the daughter cells, which, therefore, contain half the fluorescent dye compared with the parental cells (Lyons 2000). Combined with cell-surface marker staining, CFSE assay can detect the specific proliferation within the CFSE-labeled population.

Briefly, TDLNs from control and treated mice were removed on days 14 and 21 after tumor implantation. Single cell suspensions were obtained by mincing the lymph nodes in a sterile Petri dish, and the cells were washed and labeled with CFSE vital dye as described below. Briefly, cells were resuspended in 1 ml PBS containing 5 µM CFSE (Molecular Probes, Eugene, Oreg.) and incubated for 5 min at room temperature. One ml prewarmed 20% FCS in PBS was then added to each tube to remove unbound CFSE. Two×$10^6$ cells were washed twice and plated into a 24-well plate. Tumor lysate was added to reach the final concentration of 10 µg/ml as tumor antigen. Cells were collected at days 1, 2, 3 and 5 after plating, and stained with PE-anti-CD3e. FACS analysis was performed to determine the proliferation of T-cells in the presence of tumor antigen.

Morphologic and Immunohistochemical Studies

Tumors from different groups were fixed in 10% buffered formalin, embedded in paraffin, sectioned, and stained with H&E for histological examination. To perform immunohistochemical staining (IHC), tumors were snap-frozen in liquid nitrogen after immersion in O.C.T. compound (Laboratory-Tek Products, Naperville, Ill.) for frozen sectioning. Cryostat sections (5 μm) were cut, air-dried, and stored at −80° C. until used. After incubation in PBS containing 10% hydrogen peroxide at room temperature for 30 min to block endogenous peroxidase activity, frozen sections were stained with biotinylated anti-CD4 or anti-CD8 monoclonal antibodies. Sections were then incubated with HRP-conjugated streptavidin and developed with DAB (KPL, Gaithersburg, Md.) before being counterstained with Hematoxylin. Microscopic findings were recorded by an Optronix digital camera (Wetzlar, Germany) attached to a Leitz Orthoplan microscope.

Example 2

Results of B7.1-Fc and B7.2-Fc Cancer Therapy

Construction, Expression, and Purification of B7.1-Fc

The C-terminus of B7.1 extracellular domain was fused onto the N-terminus of the hinge-CH2-CH3 molecule without any linker (FIG. 1). The fused B7.1-Fc was translated under human B7.1 signal sequence and the expressed fusion protein was a dimer as shown by SDS-PAGE. Cells expressing the highest leves of B7.1-Fc fusion protein were selected using a sandwich ELISA with monoclonal antibodies against human B7.1 or human IgG Fc. This subclone was found to produce over 100 μg/ml of fusion protein in aerated stir flask cultures.

The predicated molecular weight of the expressed fusion polypeptide was confirmed by SDS-PAGE under reducing conditions. The purity of the fusion protein was confirmed by HPLC which showed a main peak with a retention time of approximately 320s. The activity of the fusion protein remains intact for one year when stored at −80° C.

Bioactivity of B7.1 Moiety of the Fusion Protein was demonstrated using a mouse T-cell proliferation assay. Anti-CD28 antibody (37.51.3 clone) was used in the same concentration as a positive control because it has been shown to activate T cells in the presence of mitogens. Plate-bound B7.1-Fc enhanced T-cell proliferation dramatically in the presence of anti-CD3, while the fusion protein alone was inactive. This demonstrated that the B7.1 extracellular domains of the B7.1-Fc fusion protein functioned as a co-stimulator.

Immunotherapy with B7.1-Fc in Colon 26 Tumor Model

The anti-tumor activity of the B7.1-Fc was studied at different doses in tumor-bearing BALB/c mice using the Colon 26 tumor model. Five days after tumor implantation, groups of mice were treated daily×5 i.v. with 40 μg, 20 μg, 10 μg, 5 μg, 1 μg, or 0.5 μg B7.1-Fc or isotype matched antibody control. At a concentration of 40 μg/day, the administration of B7.1-Fc induced complete regression of implanted tumors. Tumors in other groups treated with 20 μg to 5 μg B7.1-Fc per day also showed dramatic regressions, ranging from 76% ($P<0.01$) to 88% ($P<0.01$) reduction of tumor volume compared to control group. When the dose was decreased to 1 μg/day, there was no significant reduction of tumor volume. These studies demonstrated a dose threshold of anti-tumor effect for B7.1-Fc and B7.2-Fc treatments in this tumor model with a dramatic difference in tumor growth observed between 1 and 5 μg/dose.

A similar dose response was conduced as above but where B7.2-Fc was administered instead of B7.1-Fc. Anti-tumor effects of B7.2-Fc was comparable to that of B7.1-Fc. Both fusion proteins showed significant activity at 5 μg/dose and higher.

Combination B7.1-Fc Immunotherapy and T-cell Subset Depletion in Colon 26 Tumor Model Six-week-old female BALB/c mice were implanted with $5\times10^6$ Colon 26 s.c. and divided into five groups (n=5). One day before the tumor implantation, groups of mice are depleted of $CD4^+$, $CD8^+$, or $CD25^+$ T-cell subsets by intraperitoneal injection with appropriate antibodies. When the tumors reached 0.5 cm in diameter, B7.1-Fc treatment was initiated (20 μg dose given i.v.). Depletion of specific T-cell subsets was confirmed by flow cytometric analysis of splenocytes obtained from treated mice.

Depletion of $CD8^+$ T-cells reversed the antitumor effects of B7.1-Fc demonstrating the critical immunotherapeutic role of this T cell subset. By contrast, $CD4^+$ T-cell depletion prior to therapy had little effect. Both B7.1-Fc treatment alone and the combination treatment with anti-$CD4^+$ depletion produced a complete regression rate in 60% of the mice (3/5 mice tumor free) by day 19. $CD25^+$ T-cell depletion caused complete tumor remission of all the mice (5/5 tumor free) by day 19. The effect of T cell subset depletion on complete tumor regression using B7.1-Fc is summarized in Table 1.

TABLE 1

Combination B7.1-Fc immunotherapy with $CD4^+$, $CD8^+$, or $CD25^+$ T-cell depletion in Colon 26 tumor-bearing BALB/c mice.

| Immunotherapy Treatment | Depleted T-cell Subset | % Tumor-free Mice (complete regression)* |
| --- | --- | --- |
| Isotype control Ab (10 μg/dose) | — | 0 |
| — | CD4 | 0 |
| — | CD8 | 0 |
| — | CD25 | 0 |
| B7.1-Fc (10 μg/dose)† | — | 80 |
| B7.1-Fc (10 μg/dose)† | CD4 | 80 |
| B7.1-Fc (10 μg/dose) | CD8 | 0 |
| B7.1-Fc (10 μg/dose)† | CD25 | 100 |

*Significant differences are $0.01 < P < 0.05$ as determined by the Wilcoxon's rank-sum test.
†Rechallenge experiments were performed with these sets of mice.

Combination Immunotherapy Studies of B7.1-Fc with Different Tumor Models

Figure 2:
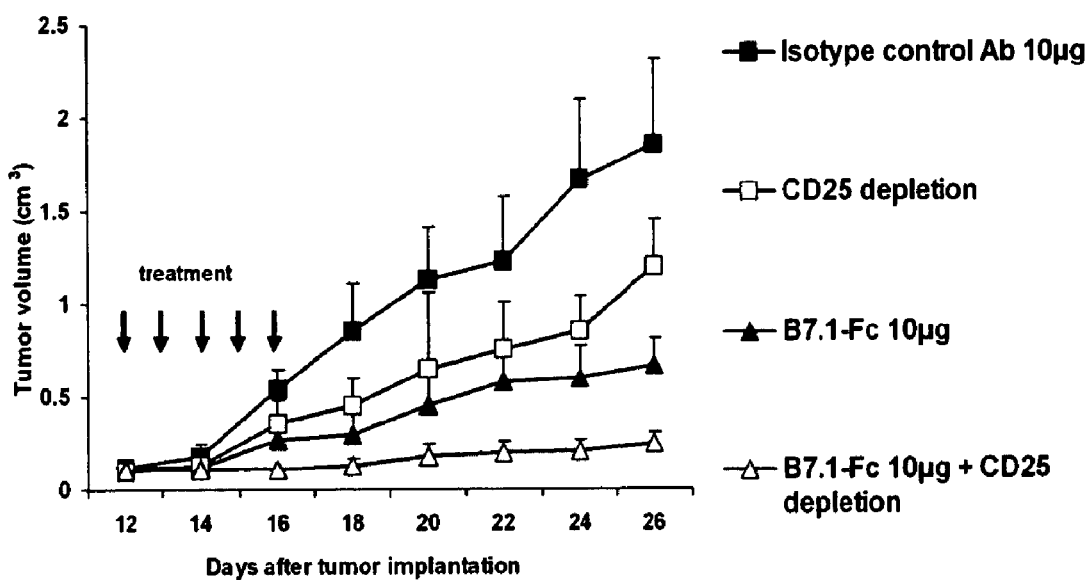
FIG. 2A-B. Shown is the effect of combination B7.1-Fc immunotherapy and $CD25^+$ T-cell depletion on the growth of growth of (2A) RENCA and (2B) MAD109 solid tumors. Six-week-old female BALB/c mice were injected with rat anti-mouse CD25 (PC-61) antibody on the day of tumor implantation on day 5, 10, and 15. Tumors were implanted s.c. using $5 \times 10^6$ RENCA cells. Treatment with B7.1-Ig started 5 days after tumor implantation when the tumors reach 0.5 cm in diameter. Treatments were administered i.v. for five consecutive days as shown by the arrows in the figure.
Figure 2:
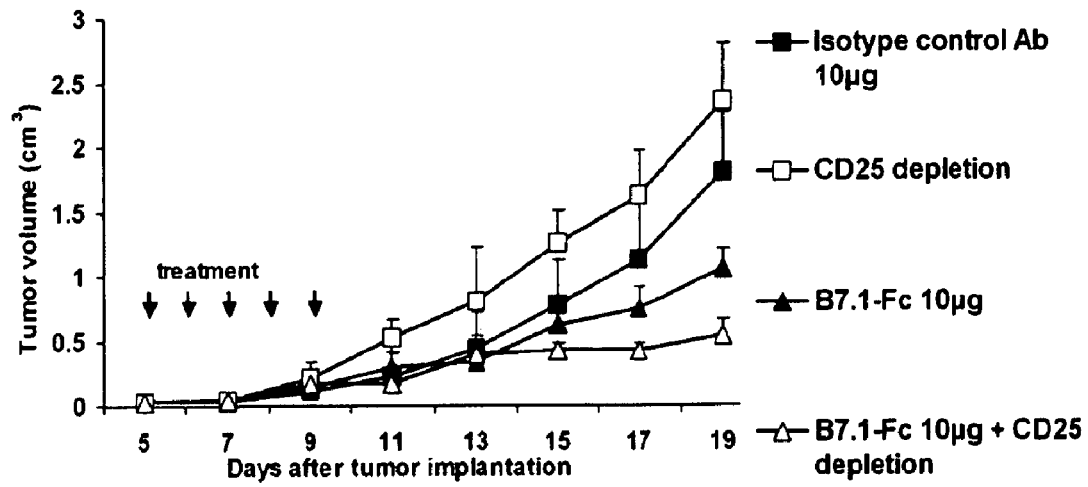
Figure 4:
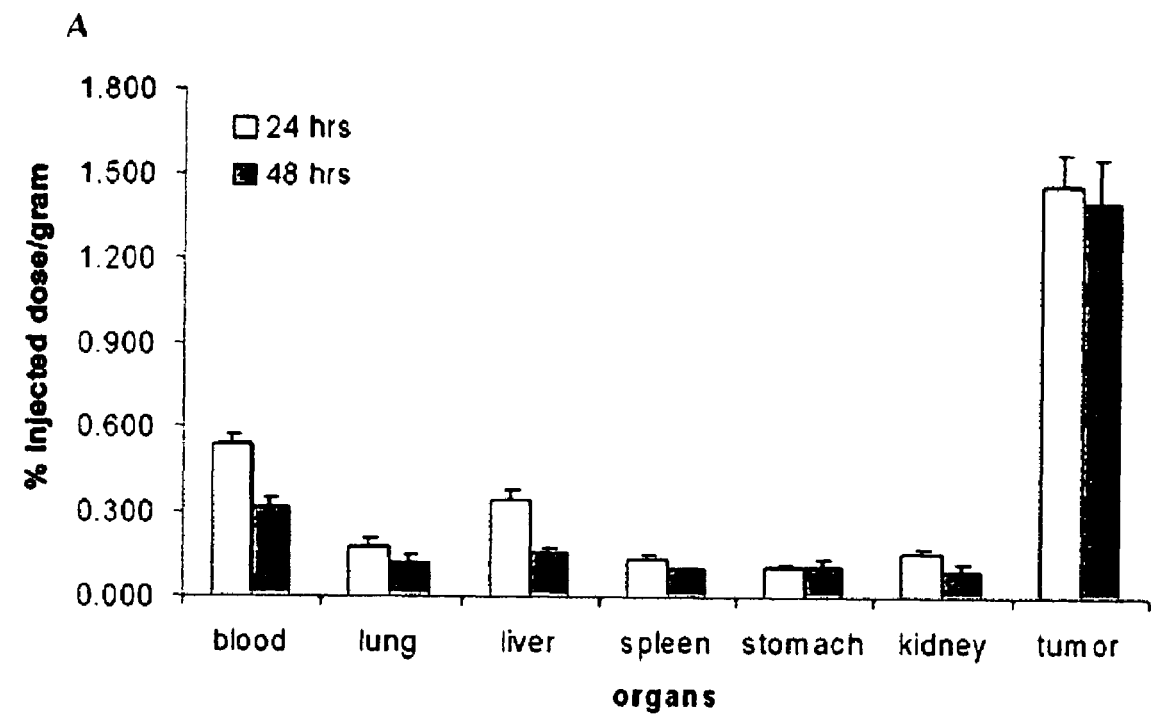
FIG. 4A-B. In vivo biodistribution of $^{125}I$-labeled B7.1/NHS76 in Colon 26-bearing BALB/c mice at 24 and 48 hours postinjection. Results were expressed for each mouse as (4A) % ID/g (percentage injected dose per gram of organ) and (4B) tumor/organ ratios.
Figure 4:
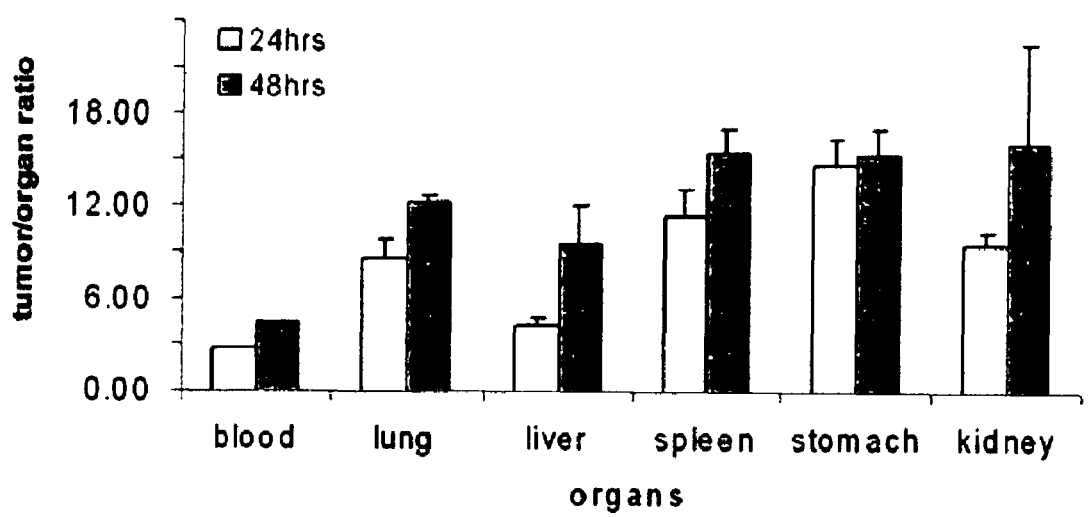

Similar studies were performed on two additional solid tumor models, including the RENCA renal carcinoma tumor and the MAD 109 lung carcinoma. For these studies, anti-CD25 was administered on the day of tumor implantation and for the next four consecutive days. FACS analysis of spleen and lymph nodes removed from these mice demonstrated essentially complete depletion of $CD25^+$ T cells. As shown in FIG. 2, combination therapy with B7.1-Fc and $CD25^+$ T-cell depletion was much better than either treatment alone. Although these data were similar to that shown in FIG. 4 above, no complete regressions were obtained in these more aggressive tumor models of the BALB/c mouse.

Tumor Rechallenge Experiments

Mice from RENCA and MAD109 tumor groups treated with B7.1-Fc and $CD25^+$ T-cell depletion which remained tumor free for two months ("tumor regressed Mice") and naïve mice were implanted with both Colon 26 and RENCA cells, or Colon 26 and MAD109 cells on contralateral flanks. For these studies, $10^6$ Colon 26 cells were s.c. implanted on the left flank, and $10^6$ RENCA or MAD109 cells were s.c. implanted on the right flank. One month after tumor implantation, all of the naïve mice were found to have solid tumors growing on their left (Colon 26) and right (RENCA or MAD109) flanks (FIG. 6), whereas the tumor regressed mice rechallenged as described rejected Colon 26 and RENCA tumors, and only had small MAD109 tumors on their right flanks. Caliper measurements of these tumors showed that their size was reduced by around 86% compared with those growing in naïve mice.

FACS Analysis of Lymphocyte Subpopulations in Tumor Sites

To determine the role of lymphocyte and dendritic cell infiltration in the tumor microenvironment, single cell suspensions of tumors removed on day 14 after tumor implantation were stained with antibody markers and analyzed by flow cytometry (FACS). The percentage of cells representing infiltrating total leukocytes in the B7.1-Fc treated groups with or without $CD25^+$ depletion (36.19% verses 47.04% respectively) was higher than the control group given isotype matched control immunoglobulin and the $CD25^+$ T-cell depletion only group (22.85% and 25.39%, respectively).

The percentage of cells representing infiltrating $CD8^+$T-cells in the B7.1-Fc treatment groups with or without $CD25^+$ depletion (4.91% and 7.91%, respectively) was greater than in the control or $CD25^+$ depletion groups (1.18% and 1%, respectively).

A similar result was also observed for infiltrating dendritic cells identified by dual staining with anti-CD11c and anti-CD11b antibodies. A greater percentage of double-positive ($CD11b^+CD11c^+$) dendritic cell infiltration was found in the B7.1-Fc treated groups with and without $CD25^+$ depletion (12.73% and 11.23%, respectively) as compared with the isotype matched control and the $CD25^+$ T-cell depleted only groups (4.59% and 6.06%, respectively).

TDLN T-cell Proliferation

To determine if the B7.1-Fc treatment also activates T-cells and if $CD25^+$ depletion affects this activation, a tumor-specific T-cell proliferation assay was performed using the vital dye, CFSE. Single cells from tumor draining lymph nodes (TDLN) were stained with CFSE, and tumor lysate (prepared from same tumor model) as a source of tumor antigens was added into the media for 24 hours before being stained with anti-CD3e antibody. Both of the control groups (isotype matched antibody group and $CD25^+$ depletion group) failed to show T-cell activation (0.06% and 0.22%, respectively). By contrast, both of the B7.1-Fc treatment groups (with and without $CD25^+$ depletion) showed T-cell activation as indicated by a significant decrease in fluorescence of the CFSE vital dye. Combination treatment, however, demonstrated a dramatically higher proliferation rate compared to B7.1-Fc treatment alone (36.62% versus 4.5%, respectively).

Histological Studies of Treated Tumors

Colon 26 tumors were harvested 5 days after completion of treatment from treated and control animals. Frozen sections of each tumor mass were stained with anti-CD4 and anti-CD8 antibodies. Light microscopic and immunohistochemical examination of tumors removed from B7.1-Fc treated mice at different time points revealed increased levels of mononuclear cell infiltrations by $CD4^+$ and $CD8^+$ cells as compared to control mice. Tumors from B7.1-Fc treated mice formed widespread multiple necrotic foci in both peri-tumoral and intra-tumoral areas. Such necrosis started early, increased in size with time, and finally led to the eventual disappearance of the tumors. This kind of tumor degeneration was distinguished from those in control tumors, which usually were found to have only one or two large necrotic areas in the central zones of tumors at advanced stages.

IFN-γ and Perforin Knockout Mice Studies and IL-4 Neutralization

The observation that B7.1-Fc-induced tumor regression was dependent on $CD8^+$ T cells raised the question as to whether interferon gamma or perforin effector arms of the $CD8^+$ CTL pathway were involved. IFN-γ is a critical cytokine for CTL differentiation and function while perforin is a downstream effector for NK and CTL function. To address this question, tumor immunotherapy with B7.1-Fc with and without $CD25^+$ Treg depletion was conducted in IFN-γ knockout and perforin knockout mice. IFN-γ deficient mice failed to reject tumors in both B7.1-Fc treatment groups, whereas perforin deficient mice showed 50% and 75% reduction in tumor size in B7.1-Fc (P<0.05) and combination treatment groups (P<0.05), respectively.

To test the roles of IL-4 in B7.1-Fc immunotherapy, IL-4 was neutralized by i.p. administration of the anti-mouse IL-4 antibody 11B11. IL-4 neutralization did not alter the anti-tumor efficacy of B7.1-FC treatment or anti-Treg combination therapy.

Example 3

Cloning and testing of B7.1/NHS76 Fusion Protein

Construction, Expression, and Purification of B7.1/NHS76 Fusion Protein

The plasmids carrying the light chain (pEE6/NHS76 A) and heavy chain (pEE12/NHS76 HC) sequences were constructed as described previously (see Sharifi, et al. 2001. *Hybridoma Hybridomics* 20:305-311). The extracellular domains of human B7.1 (Base 318-1040 Genbank: M27533) (Gordon, et al., 1989 *J. Immunol.* 143:2714-2722) were amplified by PCR from full-length cDNA of human B7.1 using primers 5'-TTC TCT AGA ATG GGC CAC ACA CGG-3' and 5'-AAT AGC GGC CGC ATC AGG AAA ATG CTC TTG-3'. The PCR product was then inserted into the N-terminus of the NHS76 HC gene in pEE12/NHS76 HC vector by XbaI and NotI under the translation of B7.1 leader sequence. B7.1 was linked at its C-terminus to the antibody variable region to preserve the activity of B7.1 which depends on its amino terminus. The resulting expression vector pEE12/B7.1/NHS76 HC was co-transfected with pEE6/NHS76 A by electroporation into NS0 cells for long-term stable expression according to the manufacturer's protocol (Lonza Biologics).

The highest producing clone was selected by an indirect ELISA assay of culture supernatant using crude DNA as antigen as previously described (Hornick, et al., 1998). Expression and purification was as described above for B7.1-Fc. After purification, the fusion protein was filtered through 0.22 μm Nalgene disposable filter unit, aliquoted, and stored at −80° C. for long-term storage in sterile 5 ml glass vials.

T-Lymphocyte Proliferation Assay

The bioactivity of B7.1 moiety was measured by modified flow cytometric method using CFSE. Briefly, a spleen was aseptically removed from a healthy BALB/c mouse and the single cell suspension was isolated by gradient centrifugation. T cells were enriched from the mononuclear cell suspension by negative adhesion with anti-mouse Ig antibody coated Petri dish. FACS analysis confirmed the purity of T-cell population to be approximate 95%. After two washes in PBS, T cells were incubated in 5 μg/ml CFSE for 5 minutes at room temperature followed by the addition of pre-warmed 10% FBS to neutralize unbound CFSE. Two×$10^6$ CFSE labeled T cells were cultured in a 24-well plate which was pre-coated with 3 μg/ml B7.1/NHS76 in the presence of 1 μg/ml plate-bound anti-CD3 (17A2 clone). After a 72-h incubation, $10^6$ cells were collected and stained with the mix of PE-anti-CD4 and anti-CD8 antibodies. CFSE intensity whose decrease reflects T-cell proliferation was analyzed by FACS. In addition, IL-2 production in the above culture supernatants was determined by a sandwich ELISA (Pepro-Tech Inc.).

Determination of Avidity Constant

To determine the avidity constant of B7.1/NHS76, a modified fixed cell radioimmunoassay (RIA) was performed in duplicate as described by Frankel and Gerhard (Frankel, et al., 1979 *Mol. Immunol.* 16: 101-106). Briefly, paraformaldehyde fixed Raji lymphoma cells containing $10^6$ cell/ml were incubated with 10 to 110 ng $^{125}$I-labeled fusion protein in 0.2 ml PBS for 1 h at room temperature with constant shaking. The cells were then washed 3× with PBS containing 1% BSA to remove unbound antibody and counted in a gamma counter. The amount of fusion protein bound was determined from the remaining cell-bound radioactivity (cpm) in each tube and the specific activity (cpm/ng) of the radiolabeled antibody. Scatchard plot analysis was performed to obtain the slope, and the avidity constant Ka was calculated by the equation $Ka=-(slope/n)$, where n is the valence of the antibody (2 for IgG).

Pharmacokinetics and Biodistribution Studies

For whole-body clearance studies, groups of six-week-old female BALB/c mice (n=5) were treated with potassium iodide in their drinking water for 1 week prior to and during the administration of radioiodine to block thyroid uptake. Each group received an intravenous injection of $^{125}$I-labeled fusion protein (30 µCi/10 µg/mouse). The whole body radioactivity of each mouse was then measured at various time intervals beginning with the immediate post-injection period using a CRC-7 microdosimeter (Capintec Inc, Pittsburg, Pa.). The data were analyzed to calculate the whole body half-life of B7.1/NHS76 as previously described (Lyons, 2000 *J. Immunol. Meth.* 243: 147-154).

For biodistribution studies, groups of BALB/c mice (n=5) were subcutaneously injected in the left flank with a 0.2 ml inoculum of $5 \times 10^6$ Colon 26 cells. The tumors were allowed to grow until the reached approximately 1 cm in diameter. Each mouse then received an i.v. injection of 0.1 ml $^{125}$I-labeled fusion protein (30 µCi/10 µg/mouse). Mice were sacrificed by sodium pentobarbital overdose at 24 and 48 h after injection, and tumors and normal organs were dissected, weighed, and measured for radioisotope activity with a gamma counter. Data were expressed for each mouse as the % injected dose/gram of tissue (% ID/g) and the tumor to normal organ ratio. From these data, the mean±standard deviation was calculated for each group. Significance levels (P values) were determined using the Wilcoxon rank-sum test.

Immunotherapy Studies

Six-week-old female BALB/c mice were subcutaneously (s.c.) injected in the left flank with a 0.2 ml inoculum containing approximately $5 \times 10^6$ Colon 26, RENCA, or MAD109 cells. Groups of mice (n=5) were intravenously (i.v.) treated with a 0.1 ml inoculum containing B7.1/NHS76 (30 µg) or control antibody NHS76 (30 µg) when the tumor reached 0.5 cm in diameter at approximately the $5^{th}$ day after tumor implantation. All groups of mice were treated daily ×5 and tumor growth was monitored every other day by caliper measurement in three dimensions. Tumor volume was calculated by the formula length×width×height. A dosing study was performed on groups of Colon 26-bearing mice treated with different doses of B7.1/NHS76 ranging from 5 µg to 120 µg daily ×5. The results were expressed as the mean±SD. Significance levels (P values) were determined using the Wilcoxon rank-sum test.

In Vivo Depletion of Lymphocyte Subsets

Antibodies were administrated on the day of tumor implantation (day 0) for $CD25^+$ T-cell depletion or the $5^{th}$ day post-tumor implantation for the depletion of the other T-cell subsets ($CD4^+$ and $CD8^+$). To deplete these T-cell subsets, 0.5 mg of anti-CD4 antibody (GK1.5), anti-CD8 antibody (H35), or anti-CD25 antibody (PC61) were injected i.p. using a 1 ml inoculum in PBS, and repeated every 5 days thereafter. Depletion of specific T-cell subsets was confirmed by FACS analyses of lymph nodes of treated mice using antibodies different from those used for depletion.

Histological Studies

Tumors from treated and control Colon 26-bearing mice were removed on days 5, 12, and 19 post-tumor implantation and evaluated by H&E staining of CD4 or CD8 IHC staining as described above for B7.1-Fc.

Example 4

Results of Immunotherapy using B7.1/NHS76 Fusion Protein

Construction, Expression, and Purification of B7.1/NHS76

Figure 3:
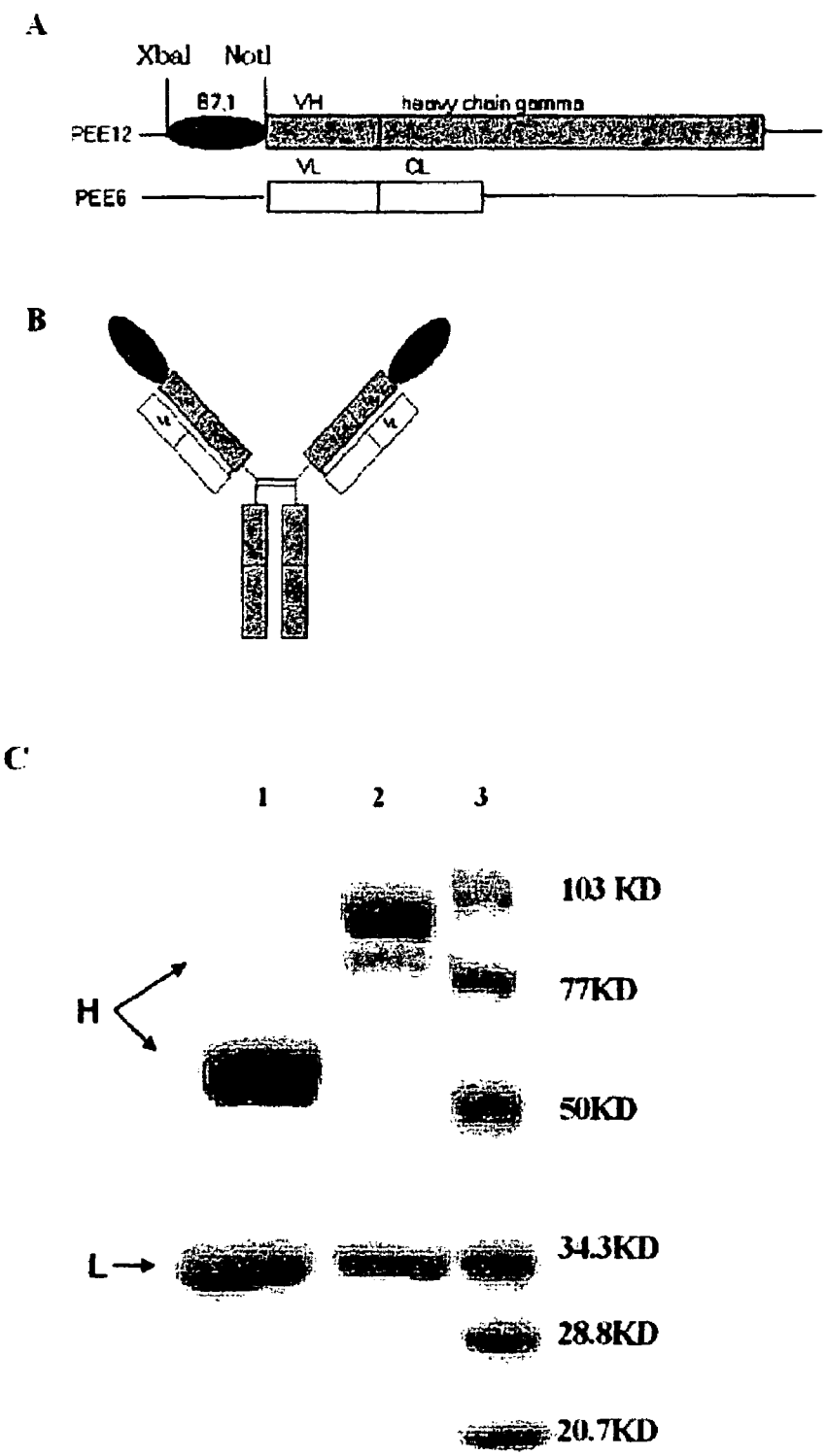
FIGS. 3A-C. 3A is a schematic diagram showing the arrangement of encoding nucleic acid for B7.1/NHS76 fusion protein. A schematic diagram of expressed B7.1/NHS76 is shown 3B. 3C is an electrophoretic analysis of NHS76 control (lane 1), B7.1/NHS76 fusion protein (lane 2), and molecular weight ladder (lane 3). Under reducing conditions, SDS-PAGE showed that the fusion protein heavy chain (H) as 100 Kd, while the NHS76 heavy chain as 56 Kd.

The C-terminus of B7.1 was linked to the N-terminus of NHS76 HC. The fused B7.1/NHS76 HC was translated under the human B7.1 signal sequence without the use of a peptide linker between the B7.1 and the NHS76 HC (FIG. 3A).

Mammalian cell NS0 expression system was used for the production of the soluble fusion protein. After subcloning twice, the highest B7.1/NHS76 producing clone was found to produce approximately 15 µg/ml/$10^6$ cells/24 h. Reducing SDS-PAGE and Western blot analysis demonstrated that the B7.1/NHS76 comprises polypeptides of 100 kD and 35 kD, corresponding close to the predicted sizes of the B7-2-fused Ig heavy chain and non-fused light chain, respectively. The higher than expected size of B7.1/NHS76 is believed to result from glycosylation of the B7.1 molecule.

Fusion of the extracellular domains of B7.1 to the variable domain of the NHS76 heavy chain did not appear to alter the secretion of the fully assembled $H_2L_2$ tetrameric form of the antibody. The structure of the expressed B7.1/NHS76 is shown schematically in FIG. 3B.

Bioactivity of B7.1 Moiety of the Fusion Protein

B7.1/NHS76 enhanced T-cell proliferation and IL-2 production in the presence of anti-CD3e compared with anti-CD3e alone. In contrast, NHS76 antibody in the presence of anti-CD3e does not increase proliferation. This shows that the B7.1 extracellular domains of the fusion protein are functional.

Binding Avidity

The binding constant Ka for B7.1/NHS76 is $2.15 \times 10^8$ $M^{-1}$ compared to $1.62 \times 10^9$ $M^{-1}$ for NHS76 (Sharifi et al., 2001). The affinity of the antibody portion of the fusion protein for TNT is about 1/7 of the parental NHS76.

In Vivo Pharmacokinetics and Biodistribution Studies

Whole-body clearance studies were performed in healthy BALB/c mice to establish the in vivo half-life of B7.1/NHS76. Uptake of the fusion protein per gram of tumor (% ID/g) was significantly higher than the normal organs ($P \leq 0.01$) at both 24 and 48 h post-injection. Rapid clearance of $^{125}$I-B7.1/NHS76 related to a marked decrease in radioactivity levels in blood, liver and kidney with time, resulting in increasing tumor-organ ratios. The results in FIG. 4 demonstrate that B7.1/NHS76 targets the tumor with good retention as compared to normal organs and blood.

Immunotherapy Studies

Five days after Colon 26 and MAD109 tumor implantation or 12 days after RENCA implantation, mice were treated daily ×5 with 30 μg B7.1/NHS76 or control NHS76. At day 14, post treatment, B7.1/NHS76-treated mice showed 35%-55% reduction in tumor growth as compared with mice treated with NHS76 (p≦0.05) in the different tumor models. Mice treated with either the fusion protein or control NHS76 showed no signs of toxicity such as loss of weight, lethargy, or ruffled fur.

Figure 5:
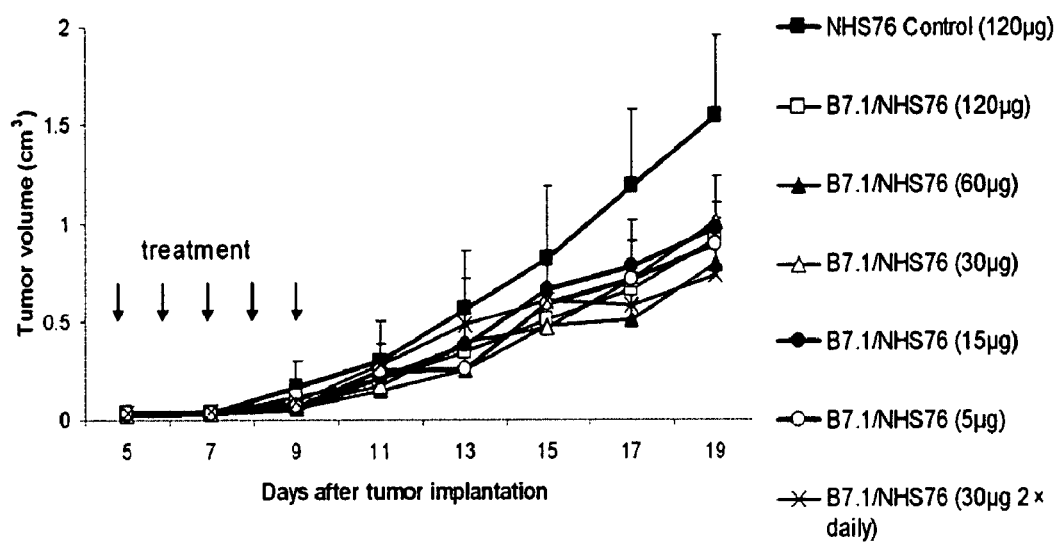
FIGS. 5A-B. 5A shows dose response of B7.1/NHS76 treatment in Colon 26-bearing BALB/c mice. B7.1/NHS76 treatment was started at $5^{th}$ day after tumor implantation with doses ranging from 5 µg to 120 µg. 5B shows combinational immunotherapy of tumor-bearing mice by B7.1/NHS76 in Colon 26 tumor models of BALB/c mice with anti-CD4, anti-CD8, or anti-CD25 antibodies.
Figure 5:
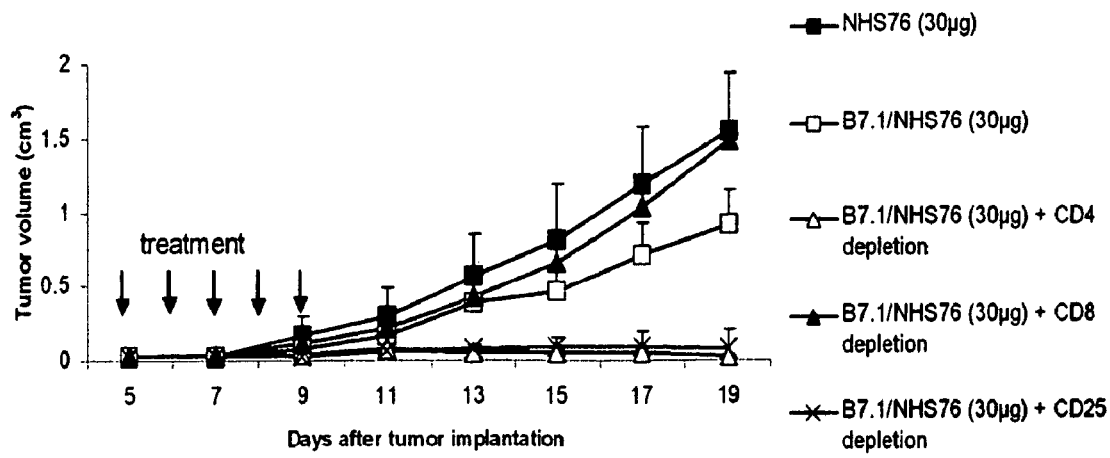

A dose response study was performed on Colon 26-bearing BALB/c mice with doses of B7.1/NHS76 from 5 μg to 120 μg (see FIG. 5A). At this range of doses, B7.1/NHS76 treatment resulted in a 35-43% reduction in tumor volume without statistically significant difference between doses (P>0.05). An increase in the frequency of administration to twice a day at 30 μg per dose gave similar results. The mice treated with any dose of fusion protein showed no signs of toxicity.

Combination Treatment Studies with Treg Cell Depletion

As shown in FIG. 5B, combination therapy with the anti-CD4 or anti-CD25 and B7.1/NHS76 treatment produced complete regression of established subcutaneous tumors. Anti-CD4 antibody (GK1.5) was initiated on the $5^{th}$ day after tumor implantation, while the anti-CD25 antibody (PC61) was begun on the same day as tumor implantation. Depletion of CD25 cells alone did not induce significant tumor regression. In addition, the anti-tumor effect of B7.1/NHS76 was shown to be $CD8^+$ T-cell dependent since $CD8^+$ depletion abrogated the anti-tumor effect.

Evaluation of Treated Tumors for Infiltrating Lymphocytes

Tumor masses from Colon 26-bearing mice that had been treated with daily×5 injections of B7.1/NHS76 were removed 5 days after the treatment and subjected to histological examination. Immunohistochemical staining of treated tumors showed moderate increases of $CD4^+$ and $CD8^+$ cell infiltration in tumors treated with B7.1/NHS76, especially $CD8^+$ T cells. The combination therapy with $CD25^+$ cell depletion further increased $CD8^+$ T cell infiltration in the tumors. It is noted that the increase of T-cell infiltration is not evident until the later time-points. Other cell populations including polymorphonuclear cells, B cells, NK cells and dendritic cells were not increased in tumors over that of the control groups.

Because B7.1 has a high affinity for CTLA-4 on T cells, B7.1-Fc blocks CTLA-4 signaling instead of cross-linking CTLA-4, thereby sustaining the activation of tumor-specific T cells or preventing their down-regulation. In addition, because the stimulation of activated T cells recognizing tumor antigens requires less costimulation, cross-linking of CD28 may be less important than blocking CTLA-4. Since B7.1-Fc was found to be capable of activating T cells in vitro and in vivo, it may have dual functions of both triggering stimulatory signals and blocking negative signals. Soluble B7.1-Fc also may act to protect dendritic cells from negative signals.

Classically, the development of highly responsive $CD8^+$ memory T cells depends on $CD4^+$ T helper cells which secrete cytokines such as IL-2 and IL-4. The results using B7.1-Fc described herein, however, show that $CD4^+$ helper T cells may not be required for the induction of effective immunotherapy.

B7.1/NHS76 was more effective than B7.1-Fc in costimulating T-cell proliferation in vitro, however, B7.1-Fc was more efficient as an anti-tumor agent in vivo.

T cells, especially $CD8^+$ CTLs, are major effector cells in tumor immunotherapy. B7.1-Fc induced dramatic increases in the infiltration of T cells not only in quantity but also in their proliferation status, as seen in the TDLN studies. It was observed that TDLNs from B7.1-Fc treated mice with and without Treg depletion were significantly bigger in size than those from control mice. In addition, tumors from B7.1-Fc treated mice showed significant widespread cell death in the tumor, which was different than that seen in control treated mice usually found to have one or two large areas of central necrosis. These results further suggest that effector T cells caused the observed tumor regression with B7.1-Fc therapy.

The synergistic cancer therapy observed from combining Treg depletion with administration of B7.1-Fc is consistent with B7.1/NHS76 and LEC/chTNT3 described previously (Li et al., *Cancer Res* 2003; 63:8384-92), but is not consistent with other cytokine fusion proteins such as IL-2, TNFα, IFNγ, and GM-CSF which were all fused to the C-terminus of a TNT type antibody (see U.S. patent publication 20040228836 and references cited therein; Sharifi et al. 2002). In addition, Treg depletion alone did not result in highly significant tumor regression.

Example 5

Construction of Fc-OX40-L (CD134-L)

The fusion protein between Fc and Ox40-L was designed so that the C-terminus of the immunoglobulin heavy chain Fc (hinge-CH2-CH3) was linked to N-terminus of the extracellular OX40L gene. Attachment to the C terminal end of OX40-L was avoided because this end is essential for bioactivity. The resulting fusion gene was cloned into pEE12 was transfected by eletroporation into NS0 cells by the Glutamine Synthetase Gene Amplification System. The best-expression clone was chosen by a sandwich ELISA assay using coated goat anti-mouse IgG/IgM and an HRP conjugated anti-mouse IgG (Fc specific) to capture the Fc fusion protein in the culture supernatant.

To produce large quantities of the fusion protein, the high-expressing clone was grown in aerated 3-L stir flasks in Selective Media containing 5% heat-inactivated dialyzed fetal calf serum to eliminate the induction of proteolytic enzymes by the NS0 cells during incubation and the breakage of the fusion protein. The secreted fusion protein was then purified from clarified cell culture supernatant by tandem protein-A affinity and ion-exchange chromatography procedures. The fusion protein appeared as a single peak by HPLC analysis.

Example 6

Immunotherapy using Fc-GITR-L

Dosing Immunotherapy Study

Figure 6:
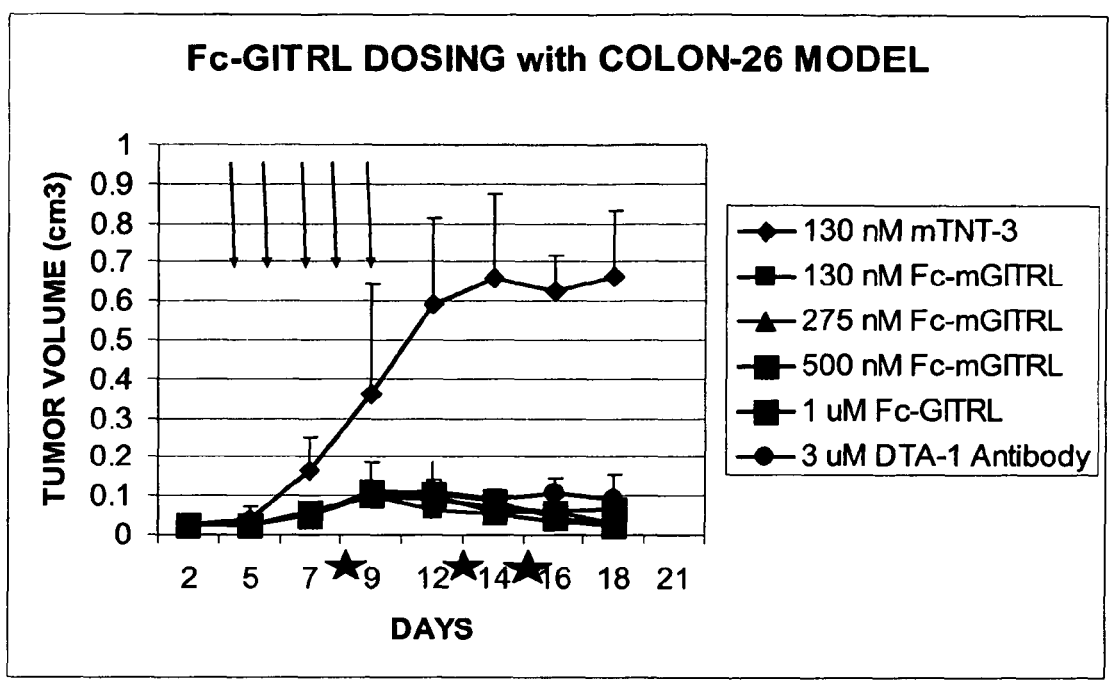
FIG. 6. Six-week old female BALB/c mice (5 per group) with 7 day subcutaneous (left flank) Colon 26 cell tumors of about 0.5 cm diameter were administered intravenously 130 nM, 275 nM, 500 nM, or 1 uM of Fc-mGITRL. As a positive control, one group was treated i.p. with 3 uM of anti-GITR antibody (DTA-1) on three occasions (indicated with a star). As a negative control, one group was treated i.p. with TNT-3 antibody every five days. Tumor volumes were then calculated and plotted with standard deviations.

Groups (n=5) of six-week old female BALB/c mice were injected subcutaneously in the left flank with a 0.2 ml inoculum containing approximately $10^7$ of Colon 26 cells. The tumors were grown for 7 days until they reached approximately 0.5 cm in diameter. Groups of tumor-bearing mice were then treated intravenously with a 0.1 ml inoculum containing either 130 nM, 275 nM, 500 nM, or 1 uM of Fc-mGITRL. As a positive control, one group was treated i.p. with 3 uM of anti-GITR antibody (DTA-1) every five days (indicated with star). The tumor growth of all groups were monitored every other day by caliper measurement. The tumor volumes were then calculated by multiplying length×width×height. The average tumor volumes were plotted with their standard deviations. The results in FIG. 6 show clear immunotherapeutic benefit at all doses.

Combinatorial Study with PC61

Figure 7:
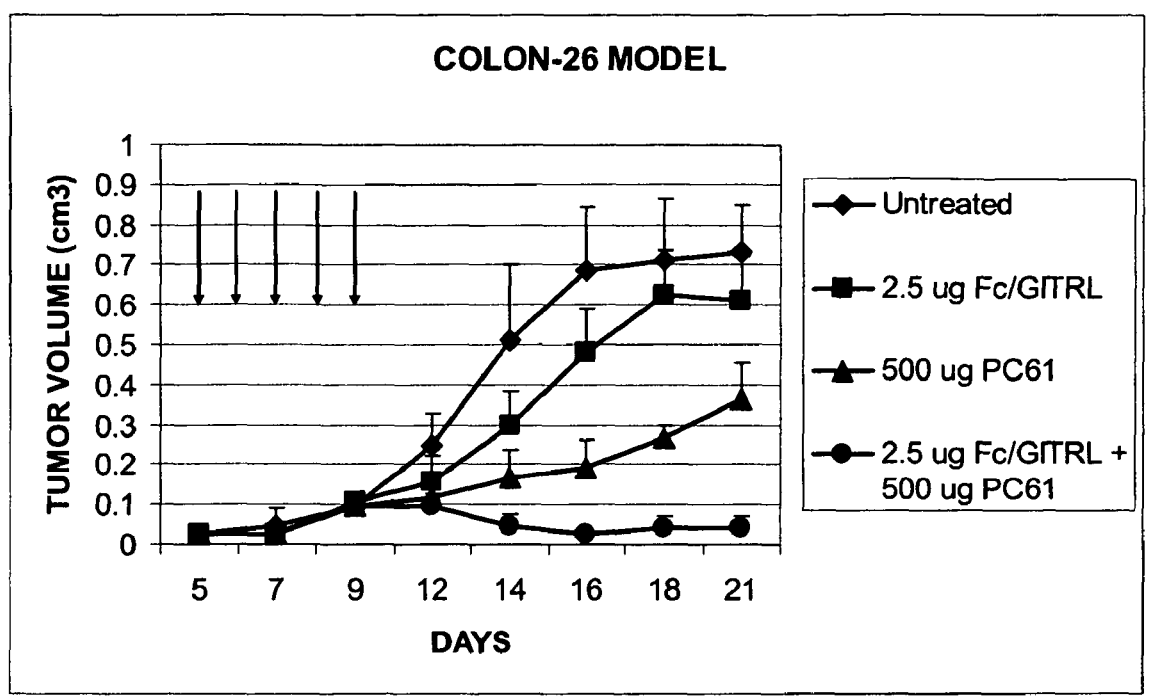
FIG. 7. Six-week old female BALB/c mice (5 per group) with 7 day subcutaneous (left flank) Colon 26 cell tumors of about 0.5 cm diameter were administered intravenously 2.5 µg of Fc/mGITRL for five consecutive days (or nothing as a negative control). On the same day as tumor implantation, one group administered intravenously 2.5 µg of Fc/mGITRL for five consecutive days also received a 0.5 mg i.p. injection of PC61 antibody (anti-CD25). Tumor volumes were then calculated and plotted with standard deviations.

Groups (n=5) of six-week old female BALB/c mice were injected subcutaneously in the left flank with a 0.2 ml inoculum containing approximately $10^7$ of Colon 26 cells. On the same day as tumor implantation, one group also received a 0.5 mg i.p. injection of PC61 antibody. The tumors were grown for 7 days until they reached approximately 0.5 cm in diameter. Groups of tumor-bearing mice were then treated intravenously with a 0.1 ml inoculum containing 2.5 µg of Fc/GITRL for five consecutive days. The tumor growth of all groups were monitored every other day by caliper measurement. The tumor volumes were then calculated by multiplying length×width×height. The average tumor volumes were plotted with their standard deviations. The results in FIG. 7 show that tumor growth for the group given 2.5 µg of Fc/GITRL and anti-CD25 antibody was much more dramatic than the group given only one of the two treatments.

REFERENCES

Aluvaihare, V R, Kallikourdis, M, and Betz, A G. Regulatory T-cells mediate maternal tolerance to the fetus. *Nature Immunol.* 5:266-271, 2004.

Blattman, J N and Greenberg, P D. Cancer immunotherapy: A treatment for the masses. *Science* 305:200-205, 2004.

Bruder, D, Probst-Kepper, M, Westendorf, A M, Geffers, R, Beissert, S, Loser, K, von Boehmer, H, Bauer, J, and Hansen, W. Neruopilin: A surface marker of regulatory T-cells. *Eur. J. Immunology* 34:623-630, 2004.

Chen, L. Co-Inhibitory molecules of the B7-CD28 family in the control of T-cell immunity. *Nature Reviews: Immunology* 4:336-347, 2004.

Curiel, T J, Coukos, G, Zou, L, Alvarez, X, Cheng, P, Mottram, P, Evdemon-Hogan, M, Conejo-Garcia, J R, Zhang, L, Burow, M, Zhu, Y, Wei, S, Kryczek, I, Daniel, B, Gordon, A, Myers, L, Lackner, A, Disis, M L, Knutson, K L, Chen, L, and Zou, W. Specific recruitment of regulatory T-cells in ovarian carcinoma fosters immune privilege and predicts reduced survival. *Nature Med.* 10:942-949, 2004.

Egen, J G, Kuhns, M S, and Allison, J R CTLA-4: New insights into its biological function and use in tumor immunotherapy. *Nature Immunol.* 3:611-618, 2002.

Fields, P E, Finch, R J, Gray, G S, Zollner, R, Thomas, J L, Sturmhoefel, K, Lee K, Wolf, S, Gajewski, T F, and Fitch, F W. B7.1 is a quantitatively stronger costimulus than B7.2 in the activation of naïve $CD8^+$ TCR-transgenic T-cells. *J. Immunol.* 161:5268-5275, 1998.

Golgher, D, Jones, E, Powrie, F, Elliott, T, and Gallimore, A. Depletion of CD25+ regulatory cells uncovers immune responses to shared murine tumor rejection antigens. *Eur. J. Immunol.* 32:3267-3275, 2002.

Hisayuki, N, Hieshima, K, Na.k.a.yama, T, Sa.k.a.guchi, T, Fujisawa, R, Tanase, S, Nishiura, H, Matsuno, K, Ta.k.a.mori, H, Tabira, Y, Yamamoto, T, Miura, R, and Yoshie, O. Human CC chemokine liver-expressed chemokine/CCL16 is a functional ligand for CCR1, CCR2, and CCR5, and constitutively expressed by hepatocytes. *Intl. Immunol.* 13:1021-1029, 2001.

Hodi, F S, Mihm, M C, Soiffer, R J, Haluska, F G, Butler, M, Seiden, M V, Davis, T, Henry-Spires, R, MacRae, S, Willman, A, Padera, R, Jaklitsch, M T, Shankar, S, Chen, T C, Korman, A, Allison, J P, and Dranoff, G. Biologic activity of cytotoxic T-lymphocyte-associated antigen 4 blockade in previously vaccinated metastatic melanoma and ovarian carcinoma patients. *Proc. Natl. Acad. Sci.* (USA) 100: 4712-4717, 2003.

Hornick, J. L., Hu, P., Khawli, L. A., Biola, B. H., Yun, A., Sharifi, J., Taylor, C. R., and Epstein, A. L. chTNT-3/B, a new chemically modified chimeric monoclonal antibody directed against DNA for the tumor necrosis treatment of solid tumors. *Cancer Biotherapy and Radiopharmaceuticals* 13:255-268, 1998.

Ichihara, F, Kono, K, Ta.k.a.hashi, A, Kawaida, H, Sugai, H, and Fujii, H. Increased populations of regulatory T-cells in peripheral blood and tumor-infiltrating lymphocytes in patients with gastric and esophageal cancers. *Clin. Cancer Res.* 9:4404-4408, 2003.

Javia, L. R. and Rosenberg, S. A. $CD4^+CD25^+$ suppressor lymphocytes in the circulation of patients immunized against melanoma antigens. *J. Immunother.* 26:85-93, 2003.

Leach, D R, Krummel, M F, and Allison, J R Enhancement of antitumor immunity by CTLA-4 blockade. *Science* 271: 1734-1736, 1996.

Li, J., Hu, P., Kwali, L., and Epstein, A. LEC/chTNT-3 fusion protein for the immunotherapy of experimental solid tumors. J. Immunother 26: 320-331, 2003.

Liyanage, U. K., Moore, T. T., Joo, H. G., Tanaka, Y., Herrmann, V., Doherty, G., Drebin, J. A., Strasberg, S. M., Eberlein, T. J., Goedegebuure, P. S., and Linehan, D. C. Prevalence of regulatory T cells is increased in peripheral blood and tumor microenvironment of patients with pancreas or breast adenocarcinoma. *J. Immunol.* 169:2756-2761, 2002.

Marshall, N A, Christie, L E, Munro, L R, Culligan, D J, Johnston, P W, Barker, R N, and Vickers, M A. Immunosuppressive regulatory T-cells are abundant in the reactive lymphocytes of Hodgkin's lymphoma. *Blood* 103:1755-1762, 2004.

McHugh, Rebecca S, Nagarajan, Shanmugam, Wang, yl-Chong, Sell, Kenneth, and Selvaraj, Perlasamy. Protein transfer of glycosylpphosphatidylinositol-B7.1 into tumor cell membranes: A novel approach to tumor immunotherapy. *Cancer Research* 59:2433-2437, 1999.

Onizuka, S., Tawara, I., Shimizu, J., Sakaguchi, S., Fujita, T., and Nakayama, E. Tumor rejection by in vivo administration of anti-CD25 (interleukin-2 receptor alpha) monoclonal antibody. *Cancer Res.* 59:3128-3133, 1999.

North, R. J. and Awwad, M. Elimination of cycling $CD4^+$ suppressor T cells with an anti-mitotic drug releases non-cycling $CD8^+$ T cells to cause regression of an advanced lymphoma. *Immunology* 71:90-95, 1990.

Pardoll, D. Does the immune system see tumors as foreign or self? *Annu. Rev. Immunol.* 21:807-839, 2003.

Parish, C R. Cancer immunotherapy: The past, the present, and the future. *Immunol. Cell Biol.* 81:106-113, 2003.

Phan, G Q, Yang, J C, Sherry, R M, Hwu, P, Topalian, S L, Schwartzentruber, D J, Restifo, N P, Haworth, L R, Seipp, C A, Freezer, L J, Morton, K E, Mavroukakis, S A, Duray, P H, Steinberg, S M, Allison, J P, Davis, T A, and Rosenberg, S A. Cancer regression and autoimmunity induced by cytotoxic T-lymphocyte-associated antigen 4 blockade in patients with metastatic melanoma. *Proc. Natl. Acad. Sci.* (USA) 100:8372-8377, 2003.

Runyon, K, Lee, K, Zuberek, K, Collins, M, Leonard, J P, and Dunussi-Joannopoulos, K. The combination of chemotherapy and systemic immunotherapy with soluble B7-immunoglobulin G leads to cure of murine leukemia and lymphoma and demonstration of tumor-specific memory responses. *Blood* 97:2420-2426, 2001.

Sakaguchi, S., Sakaguchi, N., Asano, M., Itoh, M., and Toda, M. Immunologic self-tolerance maintained by activated T cells expressing IL-2 receptor alpha-chains (CD25).

Breakdown of a single mechanism of self-tolerance causes various autoimmune diseases. *J. Immunol.* 155:1151-1164, 1995.

Shevach, E. M., McHugh, R. S., Piccirillo, C. A., and Thornton, A. M. Control of T-cell activation by CD4+ CD25+ suppressor T cells. *Immunol. Rev.* 182:58-67, 2001.

Shimizu, J., Yamazaki, S., and Sakaguchi, S. Induction of tumor immunity by removing CD25+CD4+ T cells: a common basis between tumor immunity and autoimmunity. *J. Immunol.* 163: 5211-5218, 1999.

Smyth, M J, Godfrey, D I, and Trapani, J A. A fresh look at tumor immunosurveillance and immunotherapy. *Nature Immunology* 2:293-299, 2001.

Stephens G L, McHugh, R S, Whitters, M J, Yound D A, Luxenberg, D, Carreno, B M, Collins, M, and Shevach, E M. Engagement of glucocorticoid-induced TNFR family-related receptor on effector T cells by its ligand mediates resistance to suppression by CD4+CD25+ T cells. *J. Immunology* 173:5008-5020, 2004.

Sturmhoefel, K, Lee, K, Gray, G S, Thomas, F, Zollner, R, I O'Toole, M, Swiniarski, H, Dorner, A, and Wolf, S F. Potent activity of soluble B7-IgG fusion proteins in therapy of established tumors and as vaccine adjuvant. *Cancer Res.* 59:4964-4972, 1999.

Tanaka., H., Tanaka., J., Kjaergaard, J., and Shu, S. Depletion of CD4+CD25+ regulatory cells augments the generation of specific immune T cells in tumor-draining lymph nodes. *J. Immunother.* 25: 207-217, 2002.

Waldmann, T A. Immunotherapy: Past, present, and future. *Nature Med.* 9:269-277, 2003.

Woo, E. Y., Chu, C. S., Goletz, T. J., Schlienger, K., Yeh, H., Coukos, G., Rubin, S. C., Kaiser, L. R., and June, C. H. Regulatory CD4+CD25+ T cells in tumors from patients with early-stage non-small cell lung cancer and late-stage ovarian cancer. *Cancer Res.* 61:4766-4772, 2001.

Woo, E. Y., Yeh, H., Chu, C. S., Schlienger, K., Carroll, R. G., Riley, J. L., Kaiser, L. R., and June, C. H. Cutting edge: Regulatory T cells from lung cancer patients directly inhibit autologous T cell proliferation. *J. Immunol.* 168: 4272-4276, 2002.

Yamaguchi, N, Hiraoka, S-I, Mukai, T, Takeuchi, N, Zhou, X-Y, Ono, S, Kogo, M, Dunussi-Joannopoulos, K, Ling, V, Wolf, S, and Fujiwara, H. Induction of tumor regression by administration of B7-Ig fusion proteins: Mediation by type 2 CD8+ T-cells and dependence on IL-4 production. *J. Immunol.,* 1; 172(3):1347-54, 2004.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Other embodiments are set forth within the following claims.

What is claimed is:

1. A method of reducing the size of a tumor or inhibiting the growth of cancer cells in an individual or reducing or inhibiting the development of metastatic cancer in an individual suffering from cancer, comprising
   a) administering a co-stimulatory molecule comprising a soluble form of GITR-L, said soluble form comprising one or more extracellular domains and functioning as a co-stimulator of T cell activation; and
   b) treating the individual to reduce immunoregulatory T cell activity.

2. The method of claim 1, wherein said co-stimulatory molecule is linked to another protein.

3. The method of claim 2, wherein said co-stimulatory molecule is linked to the other protein via a peptide linker.

4. The method of claim 3, wherein said linker is an immunoglobulin hinge region or portion thereof.

5. The method of claim 2, wherein said other protein is an immunoglobulin.

6. The method of claim 5, wherein reducing immunoregulatory T cell activity is achieved by using at least one antibody that binds to immunoregulatory T cells.

7. The method of claim 6, wherein said antibody is selected from the group consisting of anti-CD4, anti-CD25, anti-neuropilin, and anti-CTLA4.

8. The method of claim 2, wherein said other protein is an immunoglobulin Fc.

9. The method of claim 8, wherein reducing immunoregulatory T cell activity is achieved by using at least one antibody that binds to immunoregulatory T cells.

10. The method of claim 9, wherein said antibody is selected from the group consisting of anti-CD4, anti-CD25, anti-neuropilin, and anti-CTLA4.

11. The method of claim 2, wherein said co-stimulatory molecule is a homodimeric protein wherein each polypeptide of the homodimeric protein comprises said one or more extracellular domains of GITR-L and a hinge, CH2 and CH3 domain of an immunoglobulin.

12. The method of claim 1, wherein reducing immunoregulatory T cell activity is achieved by removing ex vivo immunoregulatory T cells from the individual.

13. The method of claim 1, wherein reducing immunoregulatory T cell activity is achieved by administering an agent to the individual that depletes or inactivates immunoregulatory T cells in the individual.

14. The method of claim 1, wherein reducing the activity of immunoregulatory T cells is achieved using at least one antibody that binds to the immunoregulatory T cells.

15. The method of claim 14, wherein said antibody is selected from the group consisting of anti-CD4, anti-CD25, anti-neuropilin, and anti-CTLA4.

16. The method of claim 1, wherein reducing the activity of immunoregulatory T cells is achieved by administering a GITR ligand agonist.

17. The method of claim 14, wherein said antibody is a murine, chimeric, humanized, or human antibody.

18. The method of claim 1, wherein reducing the activity of immunoregulatory T cells is performed before administering said co-stimulatory molecule.

19. The method of claim 1, wherein reducing the activity of immunoregulatory T cells is performed after administering said co-stimulatory molecule.

20. The method of claim 1, wherein reducing the activity of immunoregulatory T cells is performed substantially simultaneously with administering said co-stimulatory molecule.

21. The method of claim 1, further comprising administering T cells which have cytotoxic activity against the tumor or cancer cells.

22. The method of claim 21, wherein said administering T cells comprises removing T cells from the individual, activating the T cells, and then administering the activated T cells to the individual.

* * * * *

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttctctagaa tgggccacac acgg                                              24

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgtgtgagtt ttgtcatcag gaaaatgctc ttgctt                                 36

<210> SEQ ID NO 3
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 3
gagcattttc ctgatgacaa aactcacaca tgccca                                  36

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgattaatga tcaatgaatt ctcatttacc cggagacagg ga                           42

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatagcggcc gcatcaggaa aatgctcttg                                         30
```